(12) United States Patent
Grossman et al.

(10) Patent No.: US 11,033,031 B1
(45) Date of Patent: *Jun. 15, 2021

(54) BROAD SPECTRUM ANTIMICROBIAL COATINGS COMPRISING COMBINATIONS OF ORGANOSILANES

(71) Applicant: ALLIED BIOSCIENCE, INC., Plano, TX (US)

(72) Inventors: Gavri Grossman, Dallas, TX (US); Jie Fang, Carrollton, TX (US); Parham Asgari, Arlington, TX (US); Maha El-Sayed, Fremont, CA (US); Valerie Beck, Plano, TX (US); Elias Shaheen, Plano, TX (US)

(73) Assignee: ALLIED BIOSCIENCE, INC., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/200,245

(22) Filed: Mar. 12, 2021

Related U.S. Application Data

(60) Continuation of application No. 16/940,159, filed on Jul. 27, 2020, now Pat. No. 10,980,236, which is a continuation-in-part of application No. 16/591,785, filed on Oct. 3, 2019, now Pat. No. 10,993,441, which is a continuation-in-part of application No. 15/718,997, filed on Sep. 28, 2017, now Pat. No. 10,463,046, which is a division of application No. 15/041,974, filed on Feb. 11, 2016, now Pat. No. 9,918,475, which is a continuation-in-part of application No. 14/932,840, filed on Nov. 4, 2015, now Pat. No. 9,856,360.

(60) Provisional application No. 62/114,998, filed on Feb. 11, 2015, provisional application No. 62/075,020, filed on Nov. 4, 2014.

(51) Int. Cl.

| | | |
|---|---|---|
| C09D 183/08 | (2006.01) |
| A01N 55/00 | (2006.01) |
| A01N 59/16 | (2006.01) |
| A61L 2/00 | (2006.01) |
| C09D 5/14 | (2006.01) |
| A01N 25/02 | (2006.01) |
| A01N 33/08 | (2006.01) |
| B05D 1/02 | (2006.01) |
| B05D 7/14 | (2006.01) |
| B05D 7/00 | (2006.01) |
| C09D 179/02 | (2006.01) |
| C23C 26/00 | (2006.01) |
| B05D 1/04 | (2006.01) |
| C08G 77/26 | (2006.01) |
| C08K 3/22 | (2006.01) |
| C09D 183/00 | (2006.01) |

(52) U.S. Cl.
CPC ............. *A01N 55/00* (2013.01); *A01N 25/02* (2013.01); *A01N 33/08* (2013.01); *A01N 59/16* (2013.01); *A61L 2/00* (2013.01); *B05D 1/02* (2013.01); *B05D 1/04* (2013.01); *B05D 7/14* (2013.01); *B05D 7/544* (2013.01); *C08G 77/26* (2013.01); *C09D 5/14* (2013.01); *C09D 179/02* (2013.01); *C09D 183/08* (2013.01); *C23C 26/00* (2013.01); *C08K 3/22* (2013.01); *C08K 2003/2241* (2013.01); *C09D 183/00* (2013.01)

(58) Field of Classification Search
CPC .............................. C09D 183/08; C09J 83/08
See application file for complete search history.

(56) References Cited

U.S. PATENT DOCUMENTS

| | | |
|---|---|---|
| 3,044,982 A | 7/1962 | Jex et al. |
| 3,068,199 A | 12/1962 | Sellers |
| 3,133,108 A | 5/1964 | Finestone |
| 3,455,725 A | 7/1969 | Jex et al. |

(Continued)

FOREIGN PATENT DOCUMENTS

| | | |
|---|---|---|
| CN | 1597810 | 3/2005 |
| CN | 102958619 | 3/2013 |

(Continued)

OTHER PUBLICATIONS

DGIP; Notice of Allowance dated Oct. 20, 2020 in ID Application No. PID201703469.
EPO; Extended Search Report dated Oct. 21, 2020 in EP Application No. 20180203.0.
MPI; Office Action dated Oct. 29, 2020 in MX Application No. MX/a/2017/005740.
PO; Examination Report dated Dec. 31, 2020 in IN Application No. 202028017215.
USPTO; Non-Final Office Action dated Dec. 1, 2020 in U.S. Appl. No. 16/591,785.

(Continued)

*Primary Examiner* — Margaret G Moore
(74) *Attorney, Agent, or Firm* — Snell & Wilmer L.L.P.

(57) ABSTRACT

An aqueous antimicrobial coating composition capable of forming an antimicrobial coating on a surface comprises at least two organosilanes, each of the at least two organosilanes having a structure, R—Si(OR')$_3$ wherein R= —(CH$_2$)$_3$—Y; Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$; X$^-$=halide, sulfate, nitrate, phosphate, carbonate, organic sulfonate, organic carbonate, BF$_4^-$, or ClO$_4^-$; and R'=H, methyl or ethyl, or a C$_3$-C$_6$ straight-chained, branched or cyclic alkyl group, with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$.

20 Claims, 10 Drawing Sheets

(56) References Cited

U.S. PATENT DOCUMENTS

Figure 1:
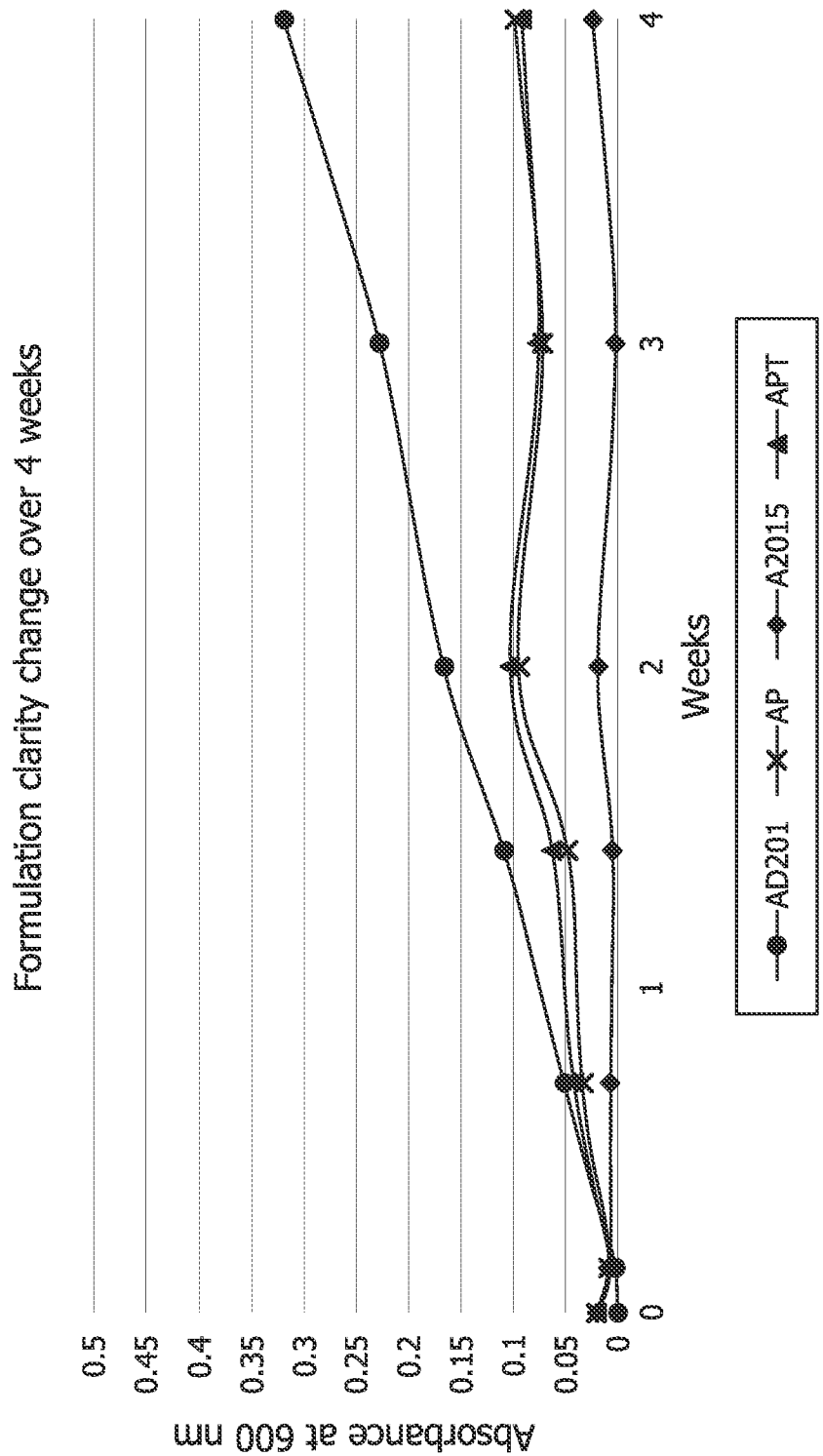

| | | | |
|---|---|---|---|
| 4,005,025 | A | 1/1977 | Kinstedt |
| 4,048,206 | A | 9/1977 | Voronkov et al. |
| 4,740,538 | A | 4/1988 | Sekutowski |
| 4,865,844 | A | 9/1989 | Blank |
| 5,359,104 | A | 10/1994 | Higgs et al. |
| 5,879,436 | A | 3/1999 | Kramer |
| 5,945,555 | A | 8/1999 | Yoshitake |
| 5,954,869 | A | 9/1999 | Elfersy |
| 5,959,014 | A | 9/1999 | Liebeskind et al. |
| 6,331,434 | B1 | 12/2001 | Decor et al. |
| 6,759,127 | B1 | 7/2004 | Smith et al. |
| 7,704,561 | B2 | 4/2010 | Mehta et al. |
| 7,884,089 | B2 | 2/2011 | Gimvang |
| 8,025,120 | B2 | 9/2011 | Eddy |
| 8,491,922 | B2 | 7/2013 | Eddy |
| 8,349,911 | B2 | 8/2013 | Kuehnle |
| 2,135,618 | A1 | 5/2014 | Ludwig et al. |
| 8,754,146 | B2 | 6/2014 | Ziolkowski |
| 8,771,315 | B2 | 7/2014 | Rodengen et al. |
| 8,790,623 | B2 | 7/2014 | Lalleman |
| 8,815,351 | B2 | 8/2014 | Owens |
| 8,859,009 | B2 | 10/2014 | Nikawa |
| 8,900,716 | B2 | 12/2014 | Hodges et al. |
| 8,951,341 | B2 | 2/2015 | Jaffrennou |
| 8,956,665 | B2 | 2/2015 | Balkan et al. |
| 8,999,357 | B2 | 4/2015 | Elfersy et al. |
| 9,028,846 | B2 | 5/2015 | Eddy |
| 9,089,138 | B2 | 7/2015 | Higgins et al. |
| 9,145,536 | B2 | 9/2015 | Adamy et al. |
| 9,265,248 | B2 | 2/2016 | Gentle et al. |
| 9,266,993 | B2 | 2/2016 | Stentrup et al. |
| 9,364,572 | B2 | 6/2016 | Peterson et al. |
| 9,445,600 | B2 | 9/2016 | Bui et al. |
| 9,458,319 | B2 | 10/2016 | Maliverney et al. |
| 9,675,735 | B2 | 6/2017 | Eddy |
| 9,717,249 | B2 | 8/2017 | Eddy |
| 10,010,080 | B2 | 7/2018 | Neigel |
| 10,072,378 | B2 | 9/2018 | Baumann |
| 10,196,559 | B1 | 2/2019 | Arvanitakis et al. |
| 10,280,315 | B2 | 5/2019 | Park et al. |
| 10,308,817 | B2 | 6/2019 | Krake et al. |
| 10,329,510 | B2 | 6/2019 | Wang et al. |
| 10,582,711 | B2 | 3/2020 | Huang |
| 10,590,284 | B2 | 3/2020 | Giovanniello |
| 10,604,729 | B2 | 3/2020 | Hawkins et al. |
| 10,640,521 | B2 | 5/2020 | Venema |
| 10,758,426 | B2 | 9/2020 | Eddy |
| 2003/0101898 | A1 | 6/2003 | Standke |
| 2005/0238839 | A1 | 10/2005 | Takagi et al. |
| 2006/0142459 | A1 | 6/2006 | Goebel |
| 2006/0269760 | A1 | 11/2006 | Sugama |
| 2007/0017567 | A1 | 1/2007 | Gronet et al. |
| 2008/0131594 | A1 | 6/2008 | Cho |
| 2009/0030220 | A1 | 1/2009 | Uchibori |
| 2009/0317624 | A1 | 12/2009 | Yoshioka |
| 2010/0029530 | A1 | 2/2010 | Whiteley |
| 2010/0234506 | A1 | 9/2010 | Elizalde |
| 2011/0000539 | A1 | 1/2011 | Gronet |
| 2011/0086567 | A1 | 4/2011 | Hawkins et al. |
| 2012/0015200 | A1 | 1/2012 | Ali |
| 2013/0040078 | A1 | 2/2013 | Scharte et al. |
| 2013/0167754 | A1 | 7/2013 | Wassmer |
| 2013/0237409 | A1 | 9/2013 | Sambandam |
| 2014/0158018 | A1 | 6/2014 | Geoffrion et al. |
| 2015/0020712 | A1 | 1/2015 | Wosyius |
| 2016/0097595 | A1 | 4/2016 | Ritchey |
| 2018/0242585 | A1 | 8/2018 | Grossman et al. |
| 2018/0280582 | A1* | 10/2018 | Grossman ............... A61L 31/08 |
| 2018/0368648 | A1 | 12/2018 | Grossman et al. |
| 2020/0068897 | A1 | 3/2020 | Grossman et al. |

FOREIGN PATENT DOCUMENTS

| | | |
|---|---|---|
| CN | 103080117 | 5/2013 |
| CN | 103305029 | 9/2013 |
| CN | 103351916 | 10/2013 |
| CN | 105461930 | 4/2016 |
| CN | 107312396 | 11/2017 |
| CN | 107903734 | 4/2018 |
| DE | 102013208034 | 11/2013 |
| EP | 1002889 | 5/2000 |
| EP | 1971206 | 9/2008 |
| EP | 1992230 | 11/2008 |
| EP | 2697422 | 4/2012 |
| EP | 3256560 | 12/2017 |
| EP | 3368600 | 9/2018 |
| GB | 1375197 | 11/1974 |
| GB | 2317178 | 3/1998 |
| IN | 270891 | 8/2006 |
| JP | 47009016 | 5/1972 |
| JP | 3311745 | 8/1991 |
| JP | 2000351940 | 12/2000 |
| JP | 2003181299 | 7/2003 |
| JP | 2004091697 | 3/2004 |
| JP | 2004204091 | 7/2004 |
| JP | 2004224861 | 8/2004 |
| JP | 2004231887 | 8/2004 |
| JP | 2004337740 | 12/2004 |
| JP | 2005131072 | 5/2005 |
| JP | 2005138059 | 6/2005 |
| JP | 2005199155 | 7/2005 |
| JP | 2005246639 | 9/2005 |
| JP | 2006136758 | 6/2006 |
| JP | 2006136782 | 6/2006 |
| JP | 3834655 | 10/2006 |
| JP | 2006526686 | 11/2006 |
| JP | 2006337740 | 12/2006 |
| JP | 2008073588 | 4/2008 |
| JP | 2008188583 | 8/2008 |
| JP | 2008276145 | 11/2008 |
| JP | 2010111793 | 5/2010 |
| JP | 201126941 | 6/2011 |
| JP | 06287068 | 5/2012 |
| JP | 2013032474 | 2/2013 |
| JP | 5881236 | 3/2016 |
| JP | 20108502975 | 2/2018 |
| JP | 2004-231887 | 4/2018 |
| KR | 1020060045901 | 5/2006 |
| KR | 1009866170000 | 10/2010 |
| RU | 2450516 | 10/1994 |
| RU | 2470053 | 12/2012 |
| SU | 0346315 | 7/1972 |
| SU | 1130570 | 12/1984 |
| SU | 1567314 | 5/1990 |
| WO | 9700134 | 1/1997 |
| WO | 2007012026 | 1/2007 |
| WO | 2007097284 | 8/2007 |
| WO | 2011059101 | 5/2011 |
| WO | 2011099510 | 8/2011 |
| WO | 2012037615 | 3/2012 |
| WO | 2012142621 | 10/2012 |
| WO | 2013082096 | 6/2013 |
| WO | 2013156327 | 10/2013 |
| WO | 2014089560 | 6/2014 |
| WO | 2016073634 | 5/2016 |

OTHER PUBLICATIONS

USPTO, Notice of Allowance dated Feb. 16, 2021 in U.S. Appl. No. 16/591,785.
MPI; Notice of Allowance dated Sep. 4, 2020 in MX Application No. MX/a/2017/008855.
DGIP; Office Action dated Sep. 23, 2020 in ID Application No. PID201704268.
DGIP; Office Action dated Jul. 23, 2020 in ID Application No. PID201704268.
MPI; Office Action dated Aug. 20, 2020 in MX Application No. MX/a/2017/005740.
DGIP; Office Action dated Aug. 24, 2020 in ID Application No. PID201703469.
USPTO; Restriction Requirement dated Aug. 25, 2020 in U.S. Appl. No. 16/591,785.

(56) References Cited

OTHER PUBLICATIONS

USPTO; Notice of Allowance dated Jun. 20, 2019 in U.S. Appl. No. 15/718,997.
PO; Examination Report dated Oct. 18, 2019 in IN Application No. 201727019302.
JPO; Office Action dated Oct. 29, 2019 in JP Application No. 2018-138257.
JPO; Notice of Allowance dated Nov. 12, 2019 in JP Application No. 2018-177318.
NIPA; Office Action dated Nov. 20, 2019 in CN Application No. 201580067821.
IPO; Office Action dated Dec. 23, 2020 in CA Application No. 2965978.
Li Shuang et al., "Preparation of Anatase TiO$_2$ Nanorods Sol by the Hydrothermal Treatment of Peroxotitanium Acid", Journal of Inorganic Materials, Aug. 2009, pp. 675-679, vol. 24, No. 4.
EUIPO;Office Action dated Feb. 3, 2020 in EP Application No. 15857660.3.
DIPO; Office Action dated Jan. 29, 2020 in ID Application No. PID201704268.
ID; Examination Report dated Mar. 31, 2020 in ID Application No. PID201703469.
JPO; Notice of Allowance dated Apr. 17, 2020 in JP Application No. 2018-138257.
EPO; Office Action dated Apr. 28, 2020 in EP Application No. 16714595.2.
NIPA; Office Action dated Jun. 11, 2020 in CN Application No. 201580067821.
CA; Office Action dated Mar. 19, 2019 in CA Application 2,965,978.
EP; Office Action dated Mar. 20, 2019 in EP Application 15 857 660.3.
CN; Non-Final Office Action dated Jun. 11, 2019 in CN Application 201580067821.
Characterization of 3-Aminopropyl Oligosilsesquioxane TP. Knepper, et al. Anal. Chern. 2016, 88, 4894-4902.
PCT; International Search Report and Written Opinion dated Feb. 23, 2016 in Application No. PCT/US2015/059080.
PCT; International Search Report and Written Opinion dated May 27, 2016 in Application No. PCT/US2016/017599.
USPTO; Restriction Requirement dated Dec. 22, 2016 in U.S. Appl. No. 14/932,840.
USPTO; Office Action dated Mar. 15, 2017 in U.S. Appl. No. 14/932,840.
USPTO; Office Action dated Apr. 3, 2017 in U.S. Appl. No. 15/432,567.
PCT; International Preliminary Report on Patentability dated May 9, 2017 in Application No. PCTIUS2015/059080.
USPTO; Restriction Requirement dated May 25, 2017 in U.S. Appl. No. 15/041,974.
USPTO; Final Office Action dated Jun. 30, 2017 in U.S. Appl. No. 15/432,567.
USPTO; Final Office Action dated Aug. 9, 2017 in U.S. Appl. No. 14/932,840.
PCT; International Preliminary Report on Patentability dated Aug. 15, 2017 in Application No. PCT/US2016/017599.
USPTO; Notice of Allowance dated Sep. 8, 2017 in U.S. Appl. No. 15/432,567.
AU; Examination Report dated Sep. 28, 2017 in Australian Application No. 2015343153.
USPTO; Notice of Allowance dated Oct. 24, 2017 in U.S. Appl. No. 14/932,840.
USPTO; Office Action dated Nov. 15, 2017 in U.S. Appl. No. 15/041,974.
USPTO; Notice of Allowance dated Jan. 3, 2018 in U.S. Appl. No. 15/041,974.
RU; Office Action dated Feb. 27, 2018 in Russian Application No. 2017117044.
AU; Examination Report No. 2 dated Mar. 1, 2018 in Austrian Application No. 2015343153.
USPTO; Office Action dated Apr. 5, 2018 in U.S. Appl. No. 15/432,428.
USPTO; Office Action dated Apr. 2, 2018 in U.S. Appl. No. 15/432,443.
USPTO; Office Action dated Apr. 12, 2018 in Canadian Application No. 2,972,923.
USPTO; Office Action dated Apr. 16, 2018 in U.S. Appl. No. 15/432,413.
USPTO; Office Action dated Apr. 25, 2018 in Japanese Patent Application No. 2017-543303.
KR; Notice of Preliminary Rejection dated May 4, 2018 in Korean Application No. 10-2017-7014833.
AU; Notice of Acceptance for Patent Application dated May 15, 2018 in Australian Application No. 2015343153.
CA; Office Action dated May 29, 2018 in Canadian Application No. 2965978.
AU; Office Action dated May 29, 2018 in Australian Application No. 2016219202.
RU; Office Action dated Jun. 15, 2018 in Russian Application No. 2017124203.
USPTO; Final Office Action dated Jul. 20, 2018 in U.S. Appl. No. 15/432,443.
USPTO; Notice of Allowance dated Aug. 22, 2018 in Japanese Application No. 2017-536331.
CA; Notice of Allowance dated Aug. 22, 2018 in Canadian Application No. 2965978.
EU; Exam Report dated Aug. 30, 2018 in European Application 15857660.3.
USPTO; Final Office Action dated Aug. 31, 2018 in U.S. Appl. No. 15/432,413.
USPTO; Final Office Action dated Aug. 31, 2018 in U.S. Appl. No. 15/432,428.
USPTO; Office Action dated Oct. 10, 2018 in Japanese Application No. 2017-543303.
KR; Final Office Action dated Oct. 18, 2018 in Korean Application No. 10-2017-7014833.
USPTO; Notice of Allowance dated Oct. 11, 2018 in U.S. Appl. No. 15/432,443.
USPTO; Non-Final Office Action dated Oct. 29, 2018 in U.S. Appl. No. 15/969,576.
USPTO; Advisory Action dated Nov. 8, 2018 in U.S. Appl. No. 15/432,428.
USPTO; Advisory Action dated Nov. 14, 2018 in U.S. Appl. No. 15/432,413.
USPTO; Notice of Allowance dated Nov. 28, 2018 in Korean Application No. 10-2017-7014833.
USPTO; Notice of Allowance dated Nov. 29, 2018 in U.S. Appl. No. 15/432,413.
USPTO; Notice of Allowance dated Dec. 26, 2018 in U.S. Appl. No. 15/432,428.
KR; Office Action dated Jan. 7, 2019 in KR Application 10-2018-7037194.
AU; Office Action dated Jan. 31, 2019 in AU Application 2018204875.
JP; Notice of Allowance dated Feb. 4, 2019 in JP Application 2017-543303.
USPTO; Notice of Allowance dated Feb. 7, 2019 in U.S. Appl. No. 15/969,576.
PCT; International Report on Patentability dated Feb. 8, 2019 in PCT Application PCT/US2018/024654.
USPTO; Non-Final Office Action dated Feb. 11, 2019 in U.S. Appl. No. 15/720,835.
USPTO; Notice of Allowance dated Feb. 19, 2019 in CA Application No. 2972923.
USPTO; Non-Final Office Action dated Feb. 25, 2019 in U.S. Appl. No. 15/718,997.
PCT; International Search Report and Written Opinion in the PCT Application No. PCT/US20/44880.
USPTO; Supplemental Notice of Allowance in the U.S. Appl. No. 16/591,785 dated Mar. 11, 2021.

* cited by examiner

BROAD SPECTRUM ANTIMICROBIAL COATINGS COMPRISING COMBINATIONS OF ORGANOSILANES

CROSS-REFERENCE TO RELATED APPLICATIONS

This application is a continuation of, claims priority to and the benefit of, U.S. application Ser. No. 16/940,159, filed Jul. 27, 2020 entitled "BROAD SPECTRUM ANTIMICROBIAL COATINGS COMPRISING COMBINATIONS OF ORGANOSILANES" (now U.S. Pat. No. 10,980,236). The '159 application is a continuation-in-part of, claims priority to and the benefit of, U.S. application Ser. No. 16/591,785, filed Oct. 3, 2019 entitled "ANTIMICROBIAL COATINGS COMPRISING ORGANOSILANE HOMOPOLYMERS." The '785 application is a continuation-in-part of U.S. application Ser. No. 15/718,997, filed Sep. 28, 2017 entitled "ANTIMICROBIAL COATINGS CAPABLE OF REDUCING THE NUMBER OF MURINE NOROVIRUS INOCULATED THEREON" (now U.S. Pat. No. 10,463,046). The '997 application is a divisional of U.S. application Ser. No. 15/041,974, filed Feb. 11, 2016 entitled "ANTI-MICROBIAL COATING AND METHOD TO FORM SAME" (now U.S. Pat. No. 9,918,475). The '974 application claims priority to U.S. Provisional Patent Application Ser. No. 62/114,998, filed Feb. 11, 2015 entitled "ANTI-MICROBIAL COATING AND METHOD TO FORM SAME." The '974 application is a continuation-in-part of U.S. application Ser. No. 14/932,840, filed Nov. 4, 2015 entitled "COMPOSITION AND METHOD TO FORM A SELF DECONTAMINATING SURFACE" (now U.S. Pat. No. 9,856,360). The '840 application claims priority to U.S. Provisional Patent Application Ser. No. 62/075,020, filed Nov. 4, 2014 entitled "COMPOSITION AND METHOD TO FORM A SELF DECONTAMINATING SURFACE." All of these disclosures are incorporated herein by reference in their entireties for all purposes.

FIELD

The present disclosure generally relates to antimicrobial coatings formed on surfaces, and more specifically, to durable antimicrobial coatings comprising organosilanes exhibiting broad spectrum residual antimicrobial efficacy.

BACKGROUND

Antimicrobial coatings formed on surfaces provide residual antimicrobial efficacy against microorganisms later inoculated onto the coating. Transfer of an organism to a surface may be through touching of the surface by a person carrying microbes, or by contamination of the surface with a biological fluid. Such antimicrobial coatings may comprise any one of a host of recognizable antimicrobial actives such as, for example, titanium dioxide ($TiO_2$), guanidine-functionalized polymers, silver and copper nanoparticles, quaternary biocide/anionic polymer complexes, essential oils, chlorine dioxide ($ClO_2$), N-halamine polymers and copolymers, antimicrobial peptides, and dimethyloctadecyl[3-(trimethoxysilyl)propyl]ammonium chloride, just to name a few. Some of these and other antimicrobial coatings are reviewed by Atul Tiwari in the book entitled, "Handbook of Antimicrobial Coatings," 2018 Elsevier Inc., ISBN 978-0-12-811982-2, which is incorporated herein by reference for all purposes.

Although many chemically diverse antimicrobial coatings are known in the industry, their ability to withstand abrasion from frequent touching (i.e., their durability) and the level of residual antimicrobial efficacy remain questionable. In fact, these two attributes often remain poor. Indeed, many known antimicrobial coatings are barely bacteriostatic in efficacy, showing no broad spectrum residual antimicrobial activity at sanitizing or disinfecting levels, and certainly no residual antiviral activity.

Therefore, a strong need still exists for invisible coatings that are easy to apply to a surface and that show both extended durability and broad spectrum efficacy against microorganisms later inoculated on the surface. In particular, durable coatings are needed that can provide broad spectrum residual antimicrobial efficacy, possibly even including antiviral efficacy against emerging pathogens.

SUMMARY

In accordance with various embodiments, it has now been discovered that antimicrobial coatings comprising certain combinations of organosilanes show both durability to repeated abrasion and broad spectrum residual antimicrobial efficacy.

In various embodiments, an aqueous antimicrobial coating composition comprises:

(a) at least two organosilanes, each of the at least two organosilanes having a structure,
$R$—$Si(OR')_3$, wherein:
$R$=—$(CH_2)_3$—$Y$;
$Y$=$^+$—$N(CH_3)_2(C_{18}H_{37})X^-$; $^+$—$N(CH_3)_2(C_{14}H_{29})X^-$; $^+$—$N(C_{10}H_{21})_2(CH_3)X^-$; —Cl or —$NH_2$;
$X^-$=halide, sulfate, nitrate, phosphate, carbonate, organic sulfonate, organic carbonate, $BF_4^-$, or $ClO_4^-$; and
$R'$=H, methyl or ethyl, or a $C_3$-$C_6$ straight-chained, branched or cyclic alkyl group with the proviso that the organosilane $R$—$Si(OR')_3$ having the $C_3$-$C_6$ straight-chained, branched or cyclic alkyl group hydrolyzes in the aqueous antimicrobial coating composition to $R$—$Si(OH)_3$; and (b) optionally, at least one organic amine having a structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12.

In various embodiments, the at least two organosilanes are selected from the group consisting of dimethyloctadecyl[3-(trihydroxysilyl)propyl]ammonium chloride (DMOD), 3-chloropropyltrimethoxysilane (CPTMS), 3-aminopropyltriethoxysilane (APTES), and mixtures thereof.

In various embodiments, the at least one organic amine is present at from about 0.01 wt. % to about 1.0 wt. %, based on the total weight of the aqueous antimicrobial coating composition.

In various embodiments, the at least one organic amine consists essentially of triethanolamine.

In various embodiments, an aqueous antimicrobial coating composition comprises from about 0.1 wt. % to about 1.0 wt. % dimethyloctadecyl[3-(trihydroxysilyl)propyl]ammonium chloride; from about 1.0 wt. % to about 15.0 wt. % 3-aminopropyltriethoxysilane; and from 0 wt. % to about 1.0 wt. % triethanolamine.

In various embodiments, an aqueous antimicrobial coating composition consists essentially of 0.5 wt. % dimethyloctadecyl[3-(trihydroxysilyl)propyl]ammonium chloride; 1.22 wt. % 3-aminopropyltriethoxysilane; remainder water.

In various embodiments, an aqueous antimicrobial coating composition consists essentially of 0.5 wt. % dimethyloctadecyl[3-(trihydroxysilyl)propyl]ammonium chloride; 2.44 wt. % 3-aminopropyltriethoxysilane; remainder water.

In various embodiments, an aqueous antimicrobial coating composition consists essentially of 0.5 wt. % dimethyloctadecyl[3-(trihydroxysilyl)propyl]ammonium chloride; 4.87 wt. % 3-aminopropyltriethoxysilane; remainder water.

In various embodiments, an aqueous antimicrobial coating composition consists essentially of 0.5 wt. % dimethyloctadecyl[3-(trihydroxysilyl)propyl]ammonium chloride; 12.18 wt. % 3-aminopropyltriethoxysilane; remainder water.

In various embodiments, an aqueous antimicrobial coating composition consists essentially of 0.75 wt. % dimethyloctadecyl[3-(trihydroxysilyl)propyl]ammonium chloride; 7.31 wt. % 3-aminopropyltriethoxysilane; remainder water.

In various embodiments, an aqueous antimicrobial coating composition consists essentially of 0.75 wt. % dimethyloctadecyl[3-(trihydroxysilyl)propyl]ammonium chloride; 7.31 wt. % 3-aminopropyltriethoxysilane; 0.045 wt. % triethanolamine; remainder water.

In various embodiments, an aqueous antimicrobial coating composition consists essentially of 0.5 wt. % dimethyloctadecyl[3-(trihydroxysilyl)propyl]ammonium chloride; 0.10 wt. % 3-chloropropyltrimethoxysilane; and 1.22 wt. % 3-aminopropyltriethoxysilane; remainder water.

In various embodiments, an aqueous antimicrobial coating composition consists essentially of 0.5 wt. % dimethyloctadecyl[3-(trihydroxysilyl)propyl]ammonium chloride; 0.10 wt. % 3-chloropropyltrimethoxysilane; and 2.44 wt. % 3-aminopropyltriethoxysilane; remainder water.

In various embodiments, an aqueous antimicrobial coating composition consists essentially of 0.5 wt. % dimethyloctadecyl[3-(trihydroxysilyl)propyl]ammonium chloride; 0.10 wt. % 3-chloropropyltrimethoxysilane; and 4.87 wt. % 3-aminopropyltriethoxysilane; remainder water.

In various embodiments, an aqueous antimicrobial coating composition consists essentially of 0.5 wt. % dimethyloctadecyl[3-(trihydroxysilyl)propyl]ammonium chloride; 0.10 wt. % 3-chloropropyltrimethoxysilane; and 12.18 wt. % 3-aminopropyltriethoxysilane; remainder water.

In various embodiments, an aqueous antimicrobial coating composition consists essentially of 0.75 wt. % dimethyloctadecyl[3-(trihydroxysilyl)propyl]ammonium chloride; 0.15 wt. % 3-chloropropyltrimethoxysilane; and 7.31 wt. % 3-aminopropyltriethoxysilane; remainder water.

In various embodiments, an aqueous antimicrobial coating composition consists essentially of 0.75 wt. % dimethyloctadecyl[3-(trihydroxysilyl)propyl]ammonium chloride; 0.15 wt. % 3-chloropropyltrimethoxysilane; 7.31 wt. % 3-aminopropyltriethoxysilane; and 0.045 wt. % triethanolamine; remainder water.

In various embodiments, an aqueous antimicrobial coating composition comprises from about 0.1 wt. % to about 1.0 wt. % dimethyloctadecyl[3-(trihydroxysilyl)propyl]ammonium chloride; from about 0.01 wt. % to about 0.5 wt. % 3-chloropropyltrimethoxysilane; and from 0 wt. % to about 1.0 wt. % triethanolamine.

In various embodiments, an aqueous antimicrobial coating composition consists essentially of 0.75 wt. % dimethyloctadecyl[3-(trihydroxysilyl)propyl]ammonium chloride; 0.12 wt. % 3-chloropropyltrimethoxysilane; 0.045 wt. % triethanolamine; remainder water.

In various embodiments, an aqueous antimicrobial coating composition consists essentially of 0.75 wt. % dimethyloctadecyl[3-(trihydroxysilyl)propyl]ammonium chloride; 0.27 wt. % 3-chloropropyltrimethoxysilane; and 0.045 wt. % triethanolamine; remainder water.

In various embodiments, an aqueous antimicrobial coating composition comprises from about 0.1 wt. % to about 1.0 wt. % dimethyloctadecyl[3-(trihydroxysilyl)propyl]ammonium chloride; from about 0.01 wt. % to about 0.5 wt. % 3-chloropropyltrimethoxysilane; from about 1.0 wt. % to about 15.0 wt. % 3-aminopropyltriethoxysilane; and from 0 wt. % to about 1.0 wt. % triethanolamine.

In various embodiments, an aqueous antimicrobial coating composition consists essentially of 0.75 wt. % dimethyloctadecyl[3-(trihydroxysilyl)propyl]ammonium chloride; 0.12 wt. % 3-chloropropyltrimethoxysilane; 7.31 wt. % 3-aminopropyltriethoxysilane; 0.045 wt. % triethanolamine; remainder water.

In various embodiments, an aqueous antimicrobial coating composition consists essentially of 0.75 wt. % dimethyloctadecyl[3-(trihydroxysilyl)propyl]ammonium chloride; 0.27 wt. % 3-chloropropyltrimethoxysilane; 7.31 wt. % 3-aminopropyltriethoxysilane; 0.045 wt. % triethanolamine; remainder water.

In various embodiments, a method of forming an antimicrobial coating on a surface comprises:

(a) applying an aqueous antimicrobial coating composition to the surface, the aqueous antimicrobial coating composition comprising:

(i) a mixture of at least two organosilanes, each of the at least two organosilanes having a structure, R—Si(OR')$_3$, wherein:

R=—(CH$_2$)$_3$—Y;

Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;

X$^-$=halide, sulfate, nitrate, phosphate, carbonate, organic sulfonate, organic carbonate, BF$_4^-$, or ClO$_4^-$; and R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$; and (ii) optionally, at least one organic amine having a structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments of the method, the at least two organosilanes are selected from the group consisting of dimethyloctadecyl[3-(trihydroxysilyl)propyl]ammonium chloride (DMOD), 3-chloropropyltrimethoxysilane (CPTMS), 3-aminopropyltriethoxysilane (APTES), and mixtures thereof.

In various embodiments of the method, the at least one organic amine is present at from about 0.01 wt. % to about 1.0 wt. %, based on the total weight of the aqueous antimicrobial coating composition.

In various embodiments of the method, the at least one organic amine consists essentially of triethanolamine.

In various embodiments of the method, the aqueous antimicrobial coating composition comprises from about 0.1 wt. % to about 1.0 wt. % dimethyloctadecyl[3-(trihydroxysilyl)propyl]ammonium chloride; from about 1.0 wt. % to about 15.0 wt. % 3-aminopropyltriethoxysilane; and from 0 wt. % to about 1.0 wt. % triethanolamine.

In various embodiments of the method, the aqueous antimicrobial coating composition comprises from about 0.1 wt. % to about 1.0 wt. % dimethyloctadecyl[3-(trihydroxysilyl)propyl]ammonium chloride; from about 0.01 wt. % to about 0.5 wt. % 3-chloropropyltrimethoxysilane; and from 0 wt. % to about 1.0 wt. % triethanolamine.

In various embodiments of the method, the aqueous antimicrobial coating composition comprises from about 0.1 wt. % to about 1.0 wt. % dimethyloctadecyl[3-(trihydroxysilyl)propyl]ammonium chloride; from about 0.01 wt. % to about 0.5 wt. % 3-chloropropyltrimethoxysilane; from about 1.0 wt. % to about 15.0 wt. % 3-aminopropyltriethoxysilane; and from 0 wt. % to about 1.0 wt. % TEA, in water.

In various embodiments of the method, the applying comprises spray application of the aqueous antimicrobial coating composition to the surface.

In various embodiments of the method, the spray application further comprises electrostatic spraying.

In various embodiments, a method of forming an aqueous antimicrobial coating composition comprises mixing at least two organosilanes in water, each of the at least two organosilanes having a structure, R—Si(OR')$_3$, wherein:
R=—(CH$_2$)$_3$—Y;
Y=$^+$—N(CH$_3$)$_2$(C$_{18}$H$_{37}$)X$^-$;  $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;
X$^-$=halide, sulfate, nitrate, phosphate, carbonate, organic sulfonate, organic carbonate, BF$_4^-$, or ClO$_4^-$; and
R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$.

In various embodiments, the method further comprises mixing at least one organic amine with the water, wherein the at least one organic amine has a structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12.

In various embodiments of the method, the at least one amine consists essentially of triethanolamine.

In various embodiments of the method, the at least two organosilanes are selected from the group consisting of dimethyloctadecyl[3-(trihydroxysilyl)propyl]ammonium chloride (DMOD), 3-chloropropyltrimethoxysilane (CPTMS), 3-aminopropyltriethoxysilane (APTES), and mixtures thereof.

In various embodiments, an antimicrobial coating is formed on a surface by a method comprising:
(a) applying an aqueous antimicrobial coating composition to the surface, the aqueous antimicrobial coating composition comprising:
(i) at least two organosilanes, each of the at least two organosilanes having a structure,
R—Si(OR')$_3$, wherein:
R=—(CH$_2$)$_3$—Y;
Y=$^+$—N(CH$_3$)$_2$(C$_{18}$H$_{37}$)X$^-$;  $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;
X$^-$=halide, sulfate, nitrate, phosphate, carbonate, organic sulfonate, organic carbonate, BF$_4^-$, or ClO$_4^-$; and
R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$; and (ii) optionally, at least one organic amine having a structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the at least two organosilanes are selected from the group consisting of dimethyloctadecyl[3-(trihydroxysilyl)propyl]ammonium chloride (DMOD), 3-chloropropyltrimethoxysilane (CPTMS), 3-aminopropyltriethoxysilane (APTES), and mixtures thereof.

In various embodiments, the aqueous antimicrobial coating composition comprises from about 0.1 wt. % to about 1.0 wt. % dimethyloctadecyl[3-(trihydroxysilyl)propyl]ammonium chloride; from about 1.0 wt. % to about 15.0 wt. % 3-aminopropyltriethoxysilane; and from 0 wt. % to about 1.0 wt. % TEA in water.

In various embodiments, the aqueous antimicrobial coating composition comprises from about 0.1 wt. % to about 1.0 wt. % dimethyloctadecyl[3-(trihydroxysilyl)propyl]ammonium chloride; from about 0.01 wt. % to about 0.5 wt. % 3-chloropropyltrimethoxysilane; from about 1.0 wt. % to about 15.0 wt. % 3-aminopropyltriethoxysilane; and from 0 wt. % to about 1.0 wt. % TEA in water.

BRIEF DESCRIPTION OF THE DRAWING FIGURES

Figure 2:
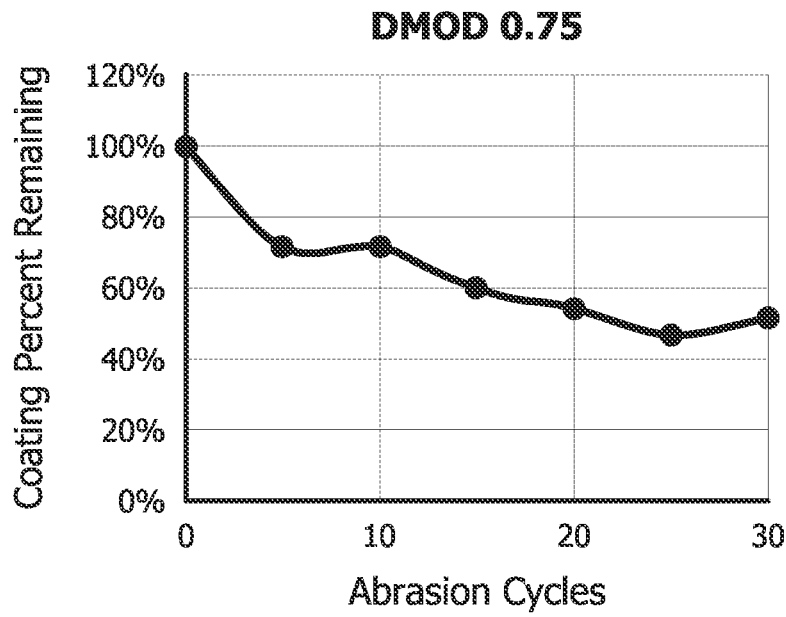
Figure 3:
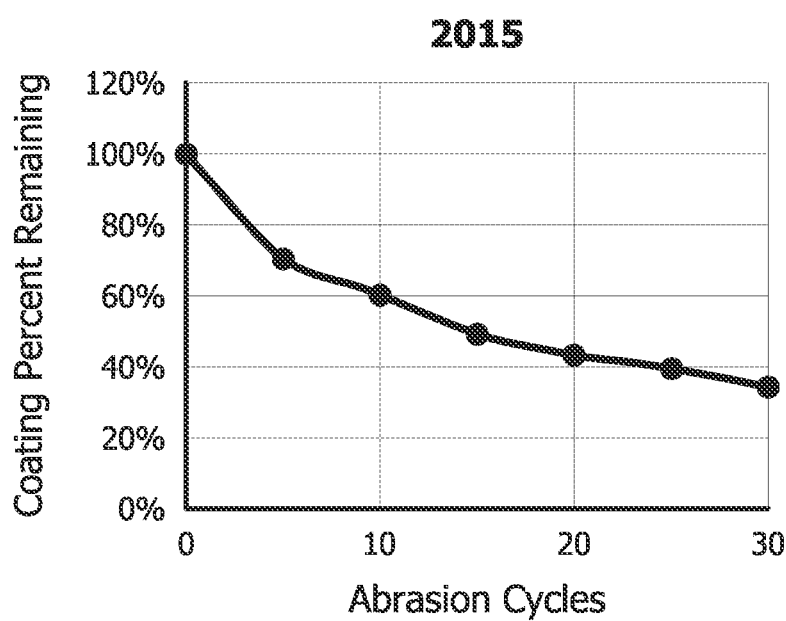
Figure 4:
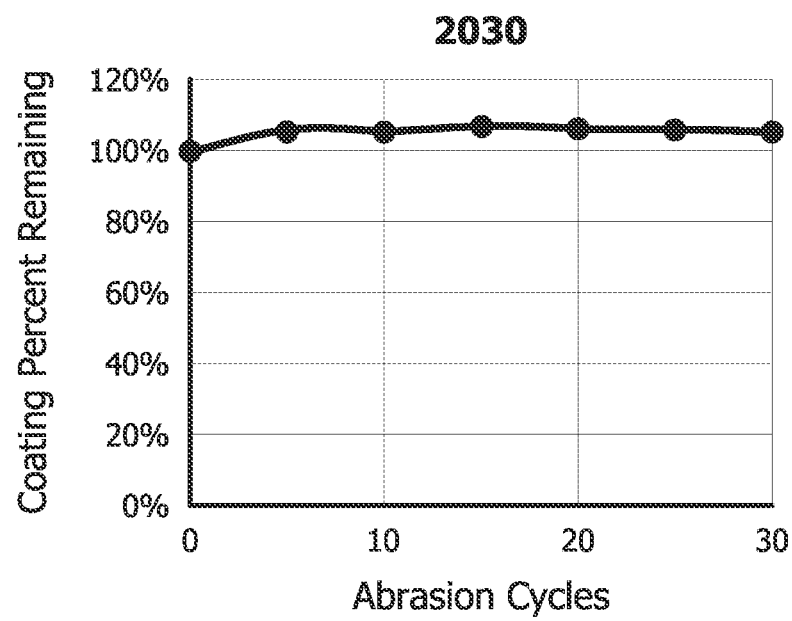
Figure 5:
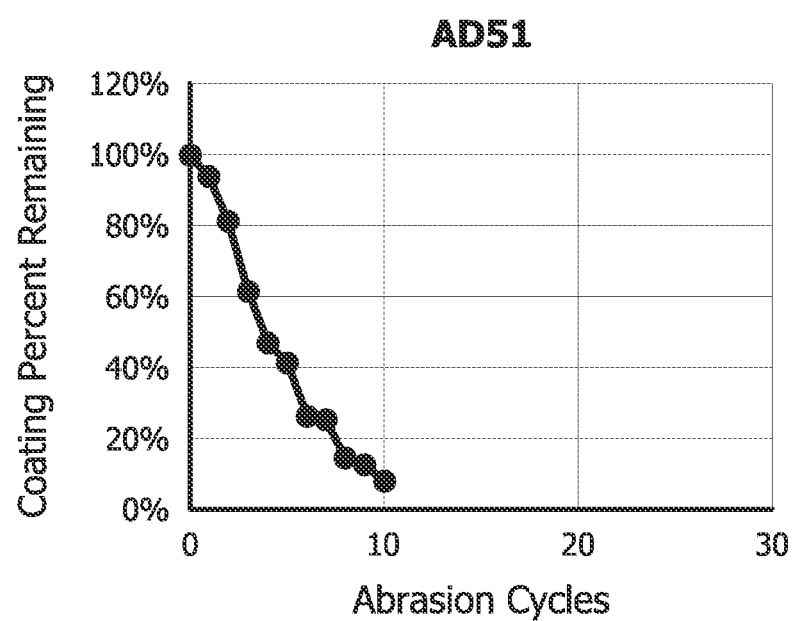
Figure 6:
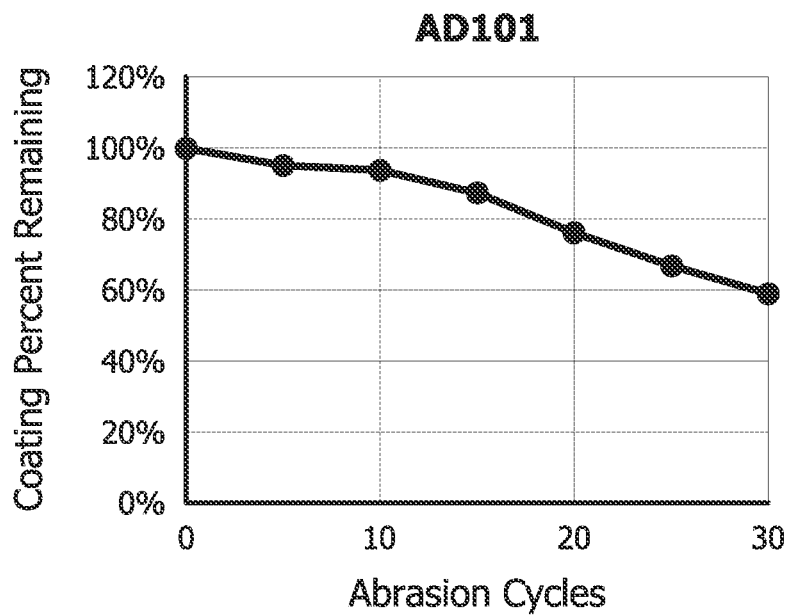
Figure 7:
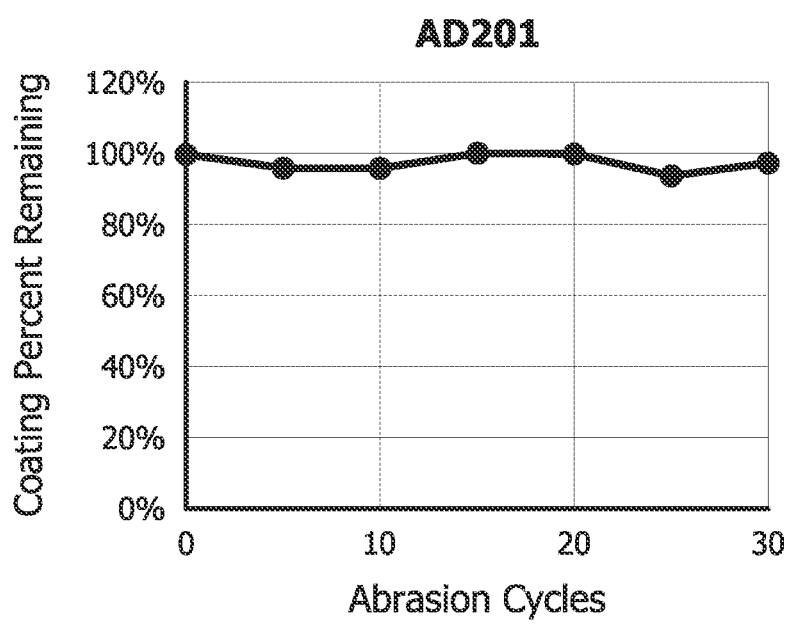
Figure 8:
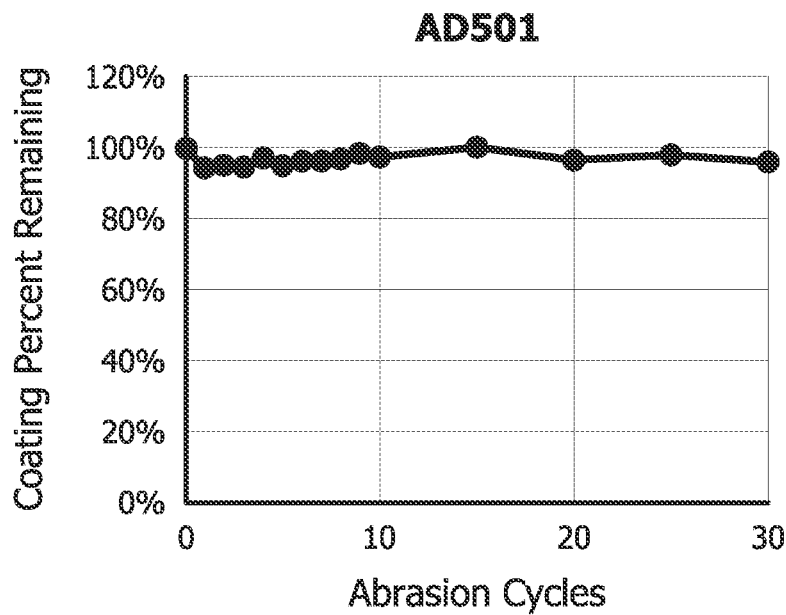
Figure 9:
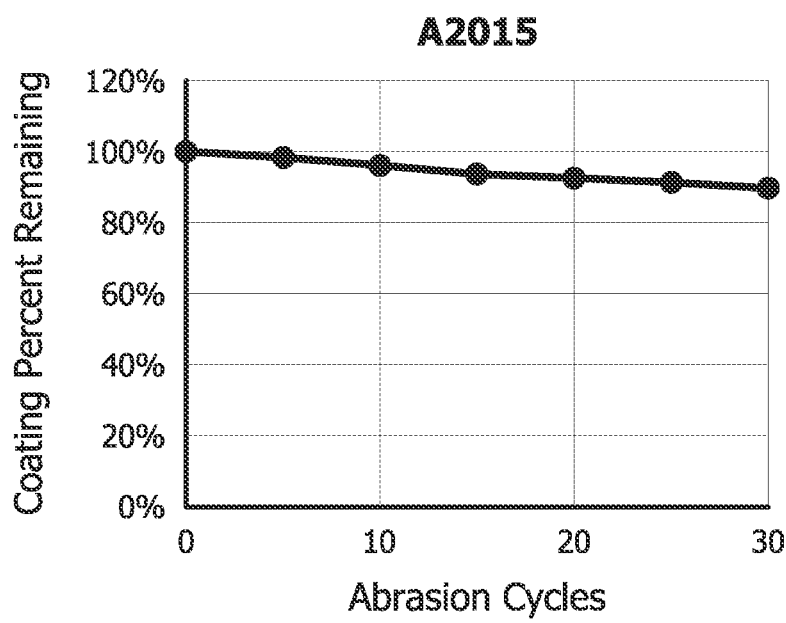
Figure 10:
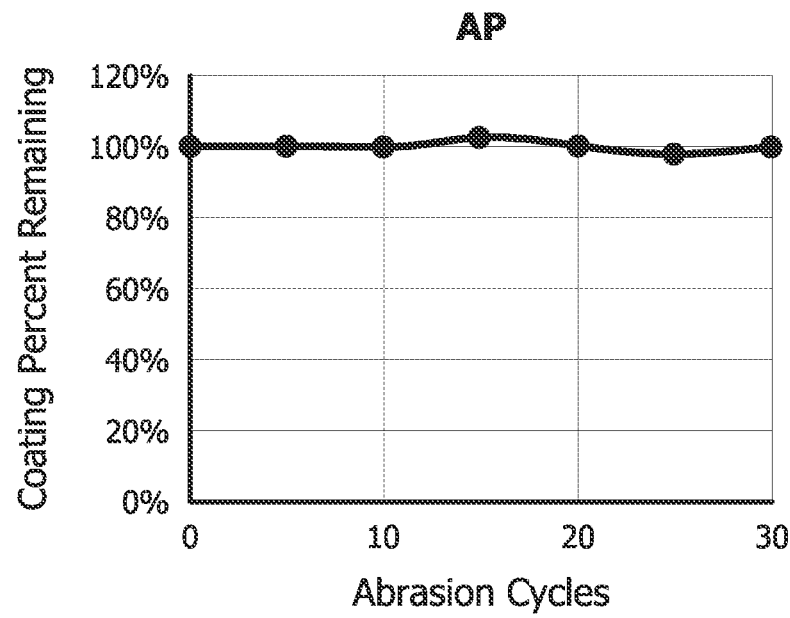
Figure 11:
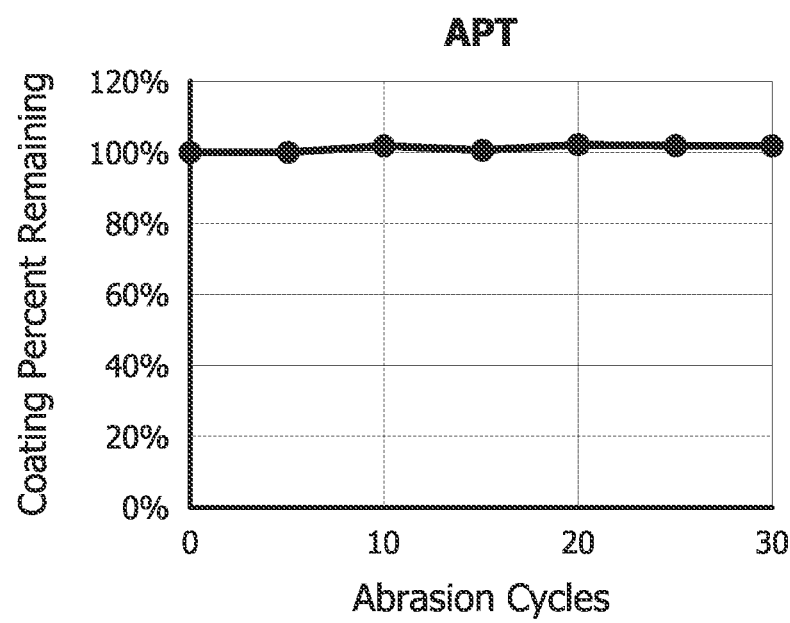
Figure 12:
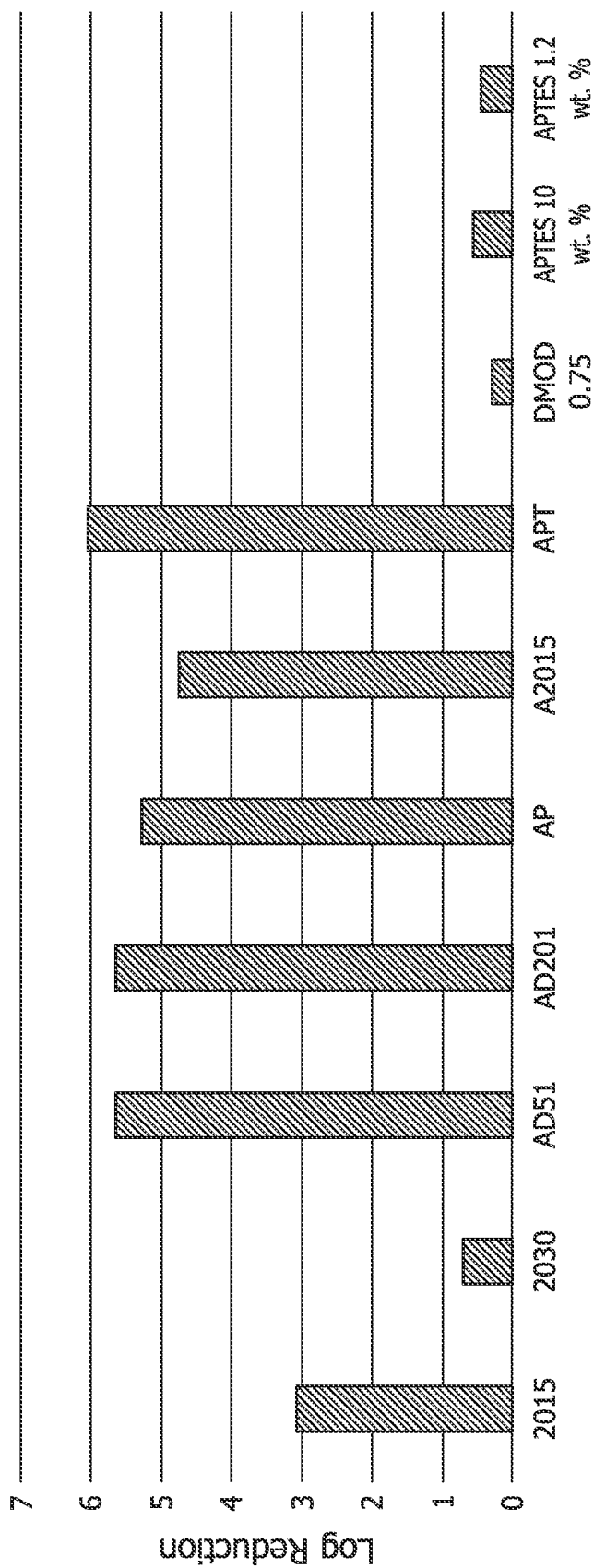
Figure 13:
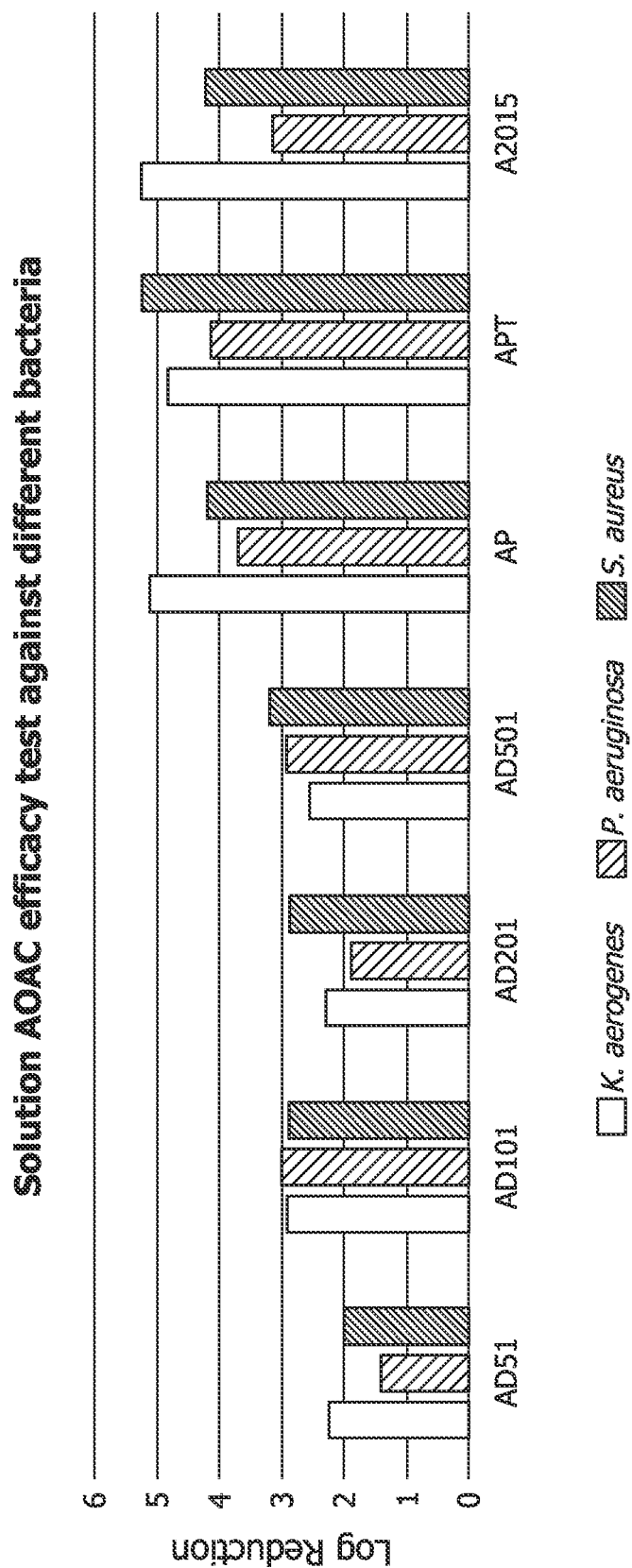
Figure 14A:
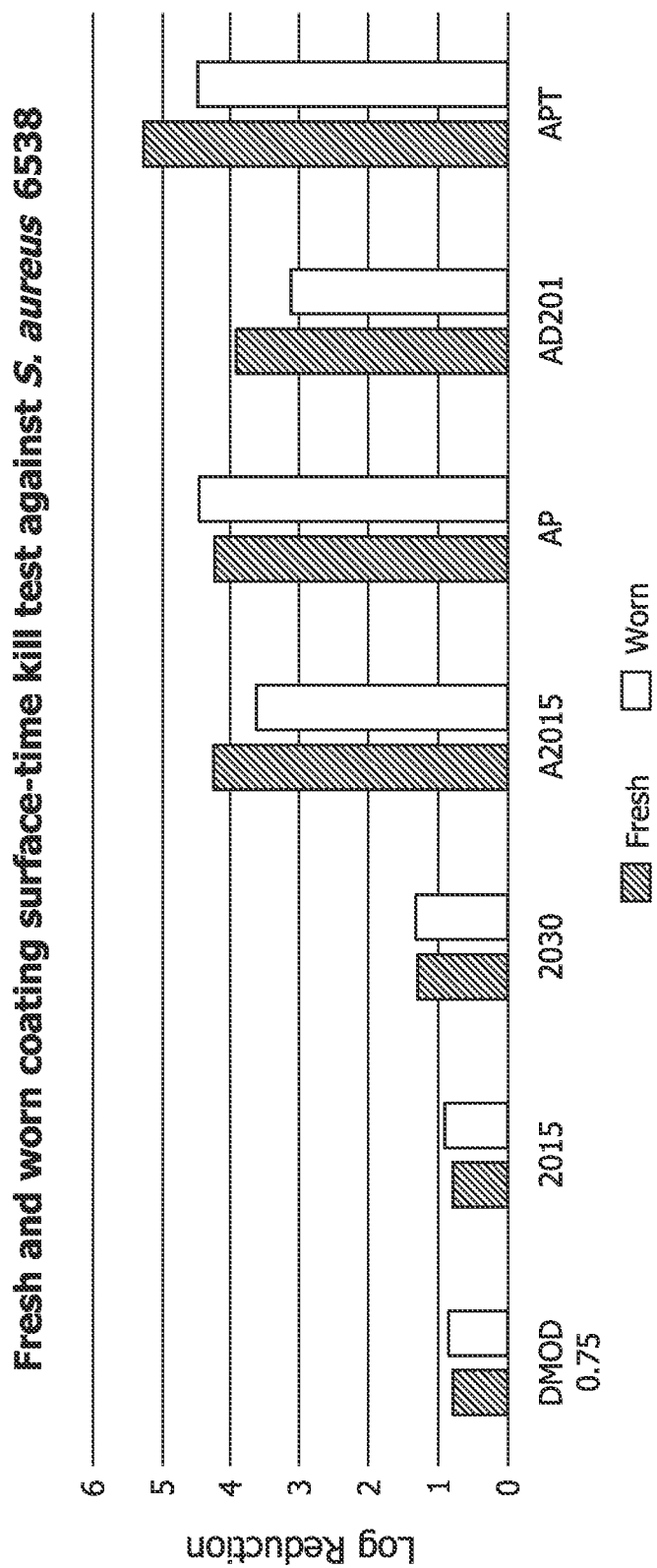
Figure 14B:
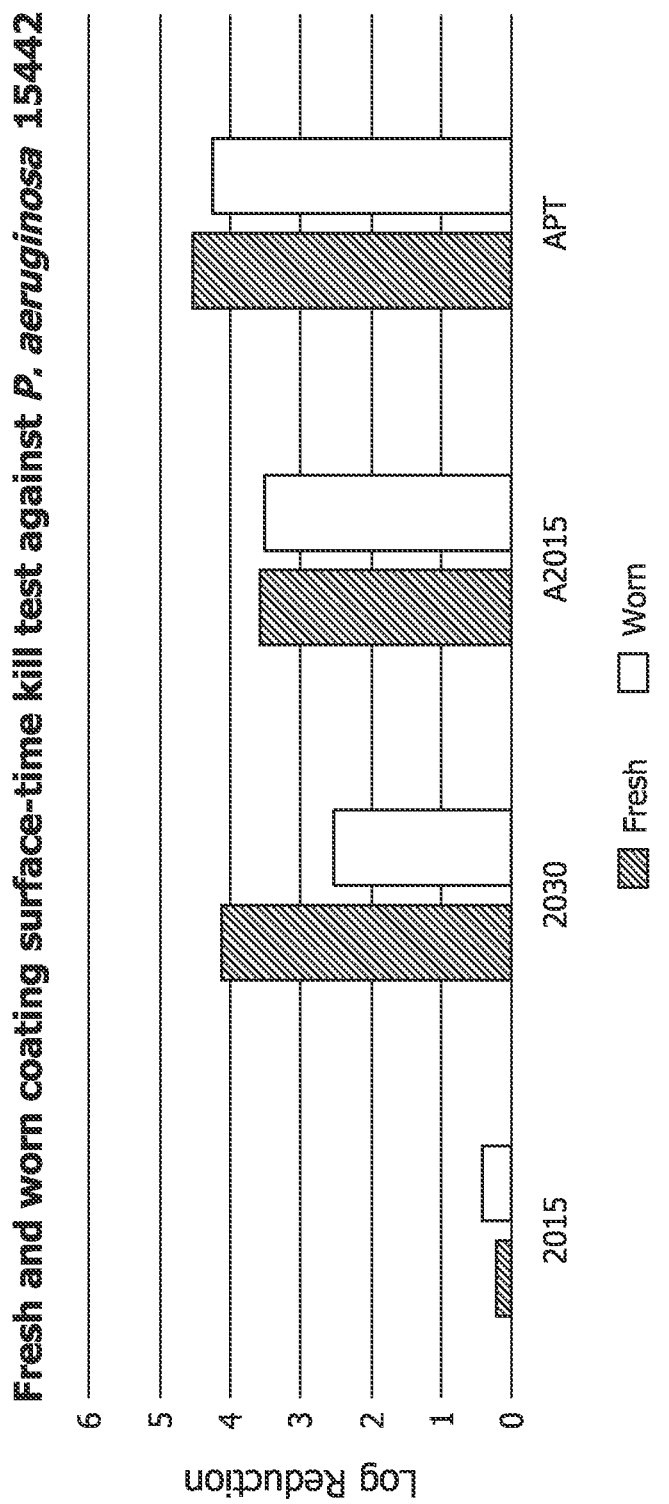

The subject matter is pointed out with particularity and claimed distinctly in the concluding portion of the specification. A more complete understanding, however, may best be obtained by referring to the detailed description and claims when considered in connection with the following drawing figures:

FIG. 1 sets forth an x/y plot of absorbance (at 600 nm) versus time as a method of measuring turbidity and assessing solution storage stability of aqueous antimicrobial coating compositions "AD201," "AP," "A2015," and "APT" from Table 1;

FIG. 2 sets forth an x/y plot of the durability to abrasion versus #abrasion cycles for an antimicrobial coating formed from a 0.75 wt. % dilution of prior art commercial DMOD;

FIG. 3 sets forth an x/y plot of the durability to abrasion versus #abrasion cycles for an antimicrobial coating formed from the composition "2015" in Table 1;

FIG. 4 sets forth an x/y plot of the durability to abrasion versus #abrasion cycles for antimicrobial coating formed from the composition "2030" in Table 1;

FIG. 5 sets forth an x/y plot of the durability to abrasion versus #abrasion cycles for an antimicrobial coating formed from the composition "AD51" in Table 1;

FIG. 6 sets forth an x/y plot of the durability to abrasion versus #abrasion cycles for an antimicrobial coating formed from the composition "AD101" in Table 1;

FIG. 7 sets forth an x/y plot of the durability to abrasion versus #abrasion cycles for an antimicrobial coating formed from the composition "AD201" in Table 1;

FIG. 8 sets forth an x/y plot of the durability to abrasion versus #abrasion cycles for an antimicrobial coating formed from the composition "AD501" in Table 1;

FIG. 9 sets forth an x/y plot of the durability to abrasion versus #abrasion cycles for an antimicrobial coating formed from the composition "A2015" in Table 1;

FIG. 10 sets forth an x/y plot of the durability to abrasion versus #abrasion cycles for an antimicrobial coating formed from the composition "AP" in Table 1;

FIG. 11 sets forth an x/y plot of the durability to abrasion versus #abrasion cycles for an antimicrobial coating formed from the composition "APT" in Table 1;

FIG. 12 sets forth sets forth a bar graph of the solution phase efficacy of various antimicrobial coating compositions from Table 1 against *S. aureus* ATCC 6538;

FIG. 13 sets forth a bar graph of the solution phase efficacy of various antimicrobial coating compositions from Table 1 against *K. aerogenes* ATCC 13048, *P. aeruginosa* ATCC 15442, and *S. aureus* ATCC 6538;

FIG. 14A sets forth a bar graph of the residual antiviral efficacy of coatings formed from various antimicrobial coating compositions in Table 1, both fresh and worn, against *S. aureus* ATCC 6538; and FIG. 14B sets forth a bar graph of the residual antiviral efficacy of coatings formed from various antimicrobial coating compositions in Table 1, both fresh and worn, against *P. aeruginosa* ATCC 15442.

DETAILED DESCRIPTION

The detailed description of exemplary embodiments makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Additionally, any reference to without contact (or similar phrases) may also include reduced contact or minimal contact.

In various embodiments, aqueous antimicrobial coating compositions, usable to produce antimicrobial coatings in the form of thin films on surfaces, comprise at least two organosilanes in combination.

In various embodiments, each of the at least two organosilanes have a structure, R—Si(OR')$_3$, wherein:
R=—(CH$_2$)$_3$—Y;
Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;
X$^-$=halide, sulfate, nitrate, phosphate, carbonate, organic sulfonate, organic carbonate, BF$_4^-$, or ClO$_4^-$; and
R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$.

In various embodiments, the aqueous antimicrobial coating compositions optionally comprise at least one organic amine. In various embodiments, the at least one organic amine fits the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises triethanolamine TEA.

In various embodiments, the aqueous antimicrobial coating compositions are optimized for storage stability. In various embodiments, preferred aqueous antimicrobial coating compositions are solution stable for at least 4-weeks at ambient temperature and humidity, with no signs of turbidity.

In various embodiments, antimicrobial coating compositions can be applied to a surface, such as by electrostatically spraying, and then dried into antimicrobial coatings in the form of thin films on the surface. The dried antimicrobial coatings thus formed exhibit at least some measure of durability and at least some degree of residual antimicrobial efficacy against certain organisms.

In various embodiments, an antimicrobial coating formed on a surface comprises at least two organosilanes in combination.

In various embodiments, each of the at least two organosilanes in the coating have a structure, R—Si(OR')$_3$, wherein:
R=—(CH$_2$)$_3$—Y;
Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;
X$^-$=halide, sulfate, nitrate, phosphate, carbonate, organic sulfonate, organic carbonate, BF$_4^-$, or ClO$_4^-$; and
R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$.

In various embodiments, the antimicrobial coating formed on a surface further comprises at least one organic amine. In various embodiments, the at least one organic amine fits the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

In various embodiments, antimicrobial coating compositions are optimized for their ability to form thin film coatings on various surfaces, such that the resulting coatings have remarkable durability against mechanical abrasion and broad spectrum residual antimicrobial efficacy.

As evident herein, only through extensive experimentation were certain combinations or organosilanes, and certain w/w ratios of those organosilanes, found to form durable antimicrobial coatings that exhibit broad spectrum residual antimicrobial efficacy.

Definitions and Interpretations

As used herein, the term "antimicrobial" is used generally to indicate at least some level of microbe kill by a composition or by a dried coating present on a surface. For example, antimicrobial may be used to indicate a biostatic efficacy, a sanitizing level (3-log, or 99.9%) reduction in at least one organism, a disinfecting level (5-log, or 99.999%) reduction in at least one organism, or sterilization (no detectable organisms). Microbes, or microorganisms, may include any species of bacteria, virus, mold, yeast, or spore. Thus, antimicrobial herein encompasses antiviral, antibacterial, antifungal, and antispore.

As used herein, the term "residual antimicrobial efficacy" refers to a characteristic shown by a dried antimicrobial coating on a surface. The characteristic or property of the coating is that the coating exhibits and maintains antimicrobial efficacy over a certain period of time under certain conditions. A coating on a surface may maintain residual antimicrobial efficacy indefinitely, or the coating may eventually "wear out" and lose its residual antimicrobial efficacy. An antimicrobial coating composition may provide a dual function in that it may first act as a contact sanitizer, disinfectant, or sterilant when applied wet to a contaminated surface, but then it may leave behind a residual antimicrobial coating on the surface once dried on that surface. The dried coating is then able to keep inactivating new microorganisms that come into contact with the coating. In various embodiments, liquid antimicrobial coating compositions may not be antimicrobial until dried on a surface, but are still referred to as "antimicrobial" coating compositions because of their ability to form a residual antimicrobial coating on a surface. Antimicrobial coating compositions for use in various embodiments may provide a coating exhibiting residual antimicrobial efficacy, meaning that a microorganism later inoculated on, or that otherwise comes into contact with, the coating on the surface may experience cell death, destruction, or inactivation. The residual antimicrobial effect made possible by the coatings herein is not limited by a particular mechanism of action, and no such theories are proffered. For example, an antimicrobial effect measured for a coating dried on a surface may be the result of intracellular mutations, inhibition of certain cellular processes, rupture of a cell wall, or a nondescript inactivation of the organism, such as in the case of viruses. Other antimicrobial effects may include inhibiting the reproduction of an organism, or inhibiting the organism's ability to accumulate into biofilms.

As used herein, the term "antimicrobial coating composition" refers to a liquid chemical composition comprising at least one chemical species in a liquid carrier such as water, which is used to produce a residual antimicrobial coating on a surface by application of the liquid composition to the surface and then drying it or allowing it to dry at ambient. The term is also used for liquid compositions that may find use as a germicidal spray (disinfectant or sanitizer), since a liquid germicidal spray composition could then go on to dry into an antimicrobial coating that exhibits residual antimicrobial efficacy as discussed above. In various embodiments, an antimicrobial coating composition may comprise a complex mixture of chemical substances, such as organosilanes and amines, some of which may chemically react (hydrolyze, self-condense, etc.) within the composition, such as with water, to produce identifiable or perhaps unidentifiable reaction products. Antimicrobial coating compositions herein may further comprise any number and combination of inert excipients, such as for example, non-aqueous solvents, buffers, acids, alkali, surfactants, emulsifiers, stabilizers, thickeners, free-radical initiators, catalysts, dyes, indicators, and the like.

As used herein, distinction is made between "ambient drying" and "heated drying." In various embodiments, aqueous antimicrobial coating compositions are applied to surfaces, such as by electrostatic spraying, and the resulting wetted surfaces are left to dry at ambient, i.e., at room temperature and humidity. In other examples, aqueous antimicrobial coating compositions applied to a surface may be heated in order to accelerate drying.

As used herein, the term "weight percent," abbreviated "wt. %," takes on the ordinary meaning of percent (%) by weight of an ingredient in a chemical composition, based on the total weight of the composition "as made." For example, an aqueous composition consisting essentially of 1.0 wt. % amine "based on the total weight of the composition" equates to a composition containing 99.0 grams water and 1.0 gram amine. Wt. % in a composition indicates the wt. % of active material, unless indicated otherwise. "As made" means that a composition as listed shows what was added to a mixing vessel and not what might end up in the mixture after certain ingredients are given sufficient time to hydrolyze or react with each other in solution, such as if an ingredient hydrolyzes, self-polymerizes, co-polymerizes, forms adducts, or is neutralized in an acid-base reaction by another ingredient.

As used herein, the acronym "q.s." used in association with an ingredient in a composition, refers to "quantity sufficient," which in formulation chemistry means that the ingredient is present in the composition in the amount necessary to total the composition to 100%.

As used herein, use of a single organosilane fitting the structure R—Si(OR')$_3$ in a composition is understood to include homologous silanes having the same R group but different R' groups such that the organosilane is capable of hydrolyzing in water to the corresponding hydrolysis product R—Si(OH)$_3$. Functional organosilanes having the general structure R—Si(OR')$_3$ are known to readily hydrolyze in water to the corresponding silanetriol R—Si(OH)$_3$ and alcohol R'OH provided the R' group is not sterically large. For example, 3-aminopropyltrimethoxysilane and 3-aminopropylsilanetriol are understood to be functional substitutes for 3-aminopropyltriethoxysilane in the aqueous compositions herein. The scope of the present disclosure also encompasses mixed alkoxysilanes where the three R' groups are not the same. Further, for organosilanes comprising a quaternary ammonium substituent, it is understood that any anionic counterion (halogens such as Cl$^-$, Br$^-$, I$^-$, inorganic or organic anions, etc.) are included in the scope of the present disclosure. When weight percentages are stated in a composition, the silane listed is either the one actually used in the composition in the amount indicated, or the silane used in the composition is "normalized" to the hydrolysis product R—Si(OH)$_3$ and that is shown in the composition.

As used herein, the shorthand "3-APTES," or more simply, "APTES," refers to 3-aminopropyltriethoxysilane. As discussed above, any hydrolysable 3-aminopropyltrialkoxysilane, or the hydrolysis product 3-aminopropylsilanetriol, can be substituted for APTES in the various compositions herein, accounting for the difference in molecular weight and adjusting weight percentage accordingly.

As used herein, the shorthand "3-CPTMS," or more simply, "CPTMS," refers to the organosilane 3-chloropropyltrimethoxysilane. As discussed above, any hydrolysable 3-chloropropyltrialkoxysilane, or the hydrolysis product 3-chloropropylsilanetriol, can be substituted for CPTMS in the various compositions herein, accounting for the difference in molecular weight and adjusting weight percentage accordingly.

As used herein, the shorthand "DMOD" refers to the organosilane dimethyloctadecyl[3-(trihydroxysilyl)propyl]ammonium chloride. As discussed above, any hydrolysable dimethyloctadecyl[3-(trialkoxysilyl)propyl]ammonium chloride can be substituted for DMOD in the various compositions herein, accounting for the difference in molecular weight and adjusting weight percentage accordingly.

As used herein, the shorthand "TEA" refers to the organic amine triethanolamine.

As used herein, the terms "carrier," "test carrier," and "coupon" are used interchangeably to mean a small test surface used to conduct various tests in a laboratory setting. In various embodiments, a carrier may comprise a 2 inch×2 inch square piece of thin 304 stainless steel. A "group of test carriers" refers to a plurality of coupons that may have been treated simultaneously in the same protocol, such as if the coupons are arranged as tiles into an array for coating as a group. Unless indicated otherwise, the term "stainless steel carrier" refers to a 304 stainless steel coupon.

As used herein, the term "fresh" refers to a carrier previously coated with an antimicrobial coating composition but not subjected to any mechanical abrasion prior to measuring residual antimicrobial efficacy of the coating.

As used herein, the term "worn" refers to a carrier previously coated with an antimicrobial coating composition and also subjected to mechanical abrasion prior to measuring residual antimicrobial efficacy of the coating. In this way, the antimicrobial efficacy of worn coatings give an indication of the durability of a coating.

As a further note, a dried antimicrobial coating may be referred to by the corresponding aqueous antimicrobial coating composition "identifier." This is for the sake of simplicity. For example, an antimicrobial coating may be referenced as "AD501," meaning that the antimicrobial coating was prepared from the AD501 aqueous antimicrobial coating composition by applying the AD501 aqueous antimicrobial coating composition to a surface and allowing the composition to dry or drying the composition. In other words, both a composition, and a dried coating resulting from the composition, may be referred to by the same name.

Aqueous Antimicrobial Coating Compositions

In various embodiments, an antimicrobial coating composition, usable in forming an antimicrobial coating on a surface, comprises a mixture of at least two organosilanes. In various embodiments, an antimicrobial coating composition comprising an aqueous coating composition in that the carrier is substantially water.

In various embodiments, each of the at least two organosilanes in an aqueous antimicrobial coating composition have a structure, R—Si(OR')$_3$, wherein:
R=—(CH$_2$)$_3$—Y;
Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;

X$^-$=halide, sulfate, nitrate, phosphate, carbonate, organic sulfonate, organic carbonate, BF$_4^-$, or ClO$_4^-$; and R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$.

In various embodiments, the at least two organosilanes are selected from the group consisting of dimethyloctadecyl[3-(trihydroxysilyl)propyl]ammonium chloride (DMOD), 3-chloropropyltrimethoxysilane (CPTMS), 3-aminopropyltriethoxysilane (APTES), and mixtures thereof.

In various embodiments, the antimicrobial coating compositions are essentially aqueous, ignoring the small amounts of methanol and/or ethanol (or other alcohols) resulting from hydrolysis of the trialkoxysilane that might be used in a composition in place of the corresponding trihydroxysilane.

In various embodiments, the antimicrobial coating compositions may be applied to surfaces and allowed to dry at ambient into thin films or dried into thin films. The resulting thin films exhibit varying degrees of residual antimicrobial efficacy and durability to mechanical abrasion.

In various embodiments, the antimicrobial coating composition further comprises at least one organic amine. In various embodiments, the at least one organic amine fits the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

In various embodiments, an antimicrobial coating composition comprises an aqueous mixture of DMOD and APTES. In various embodiments, the aqueous antimicrobial compositions further comprise at least one organic amine having the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

In various embodiments, an antimicrobial coating composition comprises an aqueous mixture of from about 0.1 wt. % to about 1.0 wt. % DMOD; from about 1.0 wt. % to about 15.0 wt. % APTES; and from 0 wt. % to about 1.0 wt. % TEA. These compositions are allowed to dry or dried on a surface to provide antimicrobial coatings in the form of thin films.

In various embodiments, an antimicrobial coating composition consists essentially of 0.5 wt. % DMOD; 1.22 wt. % APTES; remainder water. This liquid composition is referred to herein as "AD51." This composition is allowed to dry or dried on a surface to provide an antimicrobial coating in the form of a thin film.

In various embodiments, an antimicrobial coating composition consists essentially of 0.5 wt. % DMOD; 2.44 wt. % APTES; remainder water. This liquid composition is referred to herein as "AD101." This composition is allowed to dry or dried on a surface to provide an antimicrobial coating in the form of a thin film.

In various embodiments, an antimicrobial coating composition consists essentially of 0.5 wt. % DMOD; 4.87 wt. % APTES; remainder water. This liquid composition is referred to herein as "AD201." This composition is allowed to dry or dried on a surface to provide an antimicrobial coating in the form of a thin film.

In various embodiments, an antimicrobial coating composition consists essentially of 0.5 wt. % DMOD; 12.18 wt. % APTES; remainder water. This liquid composition is referred to herein as "AD501." This composition is allowed to dry or dried on a surface to provide an antimicrobial coating in the form of a thin film.

In various embodiments, an antimicrobial coating composition consists essentially of 0.75 wt. % DMOD; 7.31 wt. % APTES; remainder water. This liquid composition is referred to herein as "AP." This composition is allowed to dry or dried on a surface to provide an antimicrobial coating in the form of a thin film.

In various embodiments, an antimicrobial coating composition consists essentially of 0.75 wt. % DMOD; 7.31 wt. % APTES; 0.045 wt. % TEA; remainder water. This liquid composition is referred to herein as "APT." This composition is allowed to dry or dried on a surface to provide an antimicrobial coating in the form of a thin film.

In various embodiments, an antimicrobial coating composition comprises an aqueous mixture of DMOD and CPTMS. In various embodiments, the aqueous antimicrobial compositions further comprises at least one organic amine having the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

As indicated in the notes to Table 1, a composition listed in the table comprising both DMOD and CPTMS indicates that additional CPTMS was added to the composition, and that any trace amount of CPTMS that may have been incorporated into the composition from a particular commercial source of DMOD is ignored.

In various embodiments, an antimicrobial coating composition comprises an aqueous mixture of from about 0.1 wt. % to about 1.0 wt. % DMOD; from about 0.01 wt. % to about 0.5 wt. % CPTMS; and from 0 wt. % to about 1.0 wt. % TEA. These compositions are allowed to dry or dried on a surface to provide antimicrobial coatings in the form of thin films.

In various embodiments, an antimicrobial coating composition consists essentially of 0.75 wt. % DMOD; 0.12 wt. % CPTMS; and 0.045 wt. % TEA; remainder water. This liquid composition is referred to herein as "2015." This composition is allowed to dry or dried on a surface to provide an antimicrobial coating in the form of a thin film.

In various embodiments, an antimicrobial coating composition comprises an aqueous mixture of DMOD, CPTMS, and APTES. In various embodiments, the aqueous antimicrobial compositions further comprise at least one organic amine having the structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

Antimicrobial coating compositions comprising all three of these specific organosilanes are the result of mixing together DMOD, APTES and CPTMS (in the corresponding wt. % amount indicated in the composition). As mentioned, the trace amount of CPTMS that might be brought into the composition from the commercial DMOD source is ignored.

In various embodiments, an antimicrobial coating composition comprises an aqueous mixture of from about 0.1 wt. % to about 1.0 wt. % DMOD; from about 0.01 wt. % to about 0.5 wt. % CPTMS; from about 1.0 wt. % to about 15.0 wt. % APTES; and from 0 wt. % to about 1.0 wt. % TEA. These compositions are allowed to dry or dried on a surface to provide antimicrobial coatings in the form of thin films.

In various embodiments, an antimicrobial coating composition consists essentially of 0.75 wt. % DMOD; 0.12 wt. % CPTMS; 7.31 wt. % APTES; 0.045 wt. % TEA; remainder water. This liquid composition is referred to herein as "A2015." This composition is dried on a surface to provide an antimicrobial coating in the form of a thin film.

Screening Aqueous Antimicrobial Coating Compositions

Table 1 sets forth nine (9) antimicrobial coating compositions in accordance with the present disclosure, which are usable in preparing dried antimicrobial coatings on surfaces, wherein the resulting coatings are tested for abrasion resistance and residual antimicrobial efficacy. The antimicrobial coating compositions appearing in Table 1, while still in liquid form "as made," can be evaluated for both storage stability and antimicrobial efficacy as a contact spray sanitizer or disinfectant. Table 1 also includes three "reference" compositions, namely DMOD 0.75, APTES 1.2 and APTES 10 as shown, which are simple dilutions of single organosilane in water.

As these and other compositions were made and tested, unusual and unexpected results were seen in storage stability of the liquid compositions, and the durability and residual antimicrobial efficacy of the dried coatings resulting from the compositions. In particular, the synergy between DMOD and APTES, discussed in more detail herein below, was surprising and unexpected.

TABLE 1

Antimicrobial Coating Compositions (as made)

| Formulation Identifier | Ingredient (wt. %) | | | | |
|---|---|---|---|---|---|
| | DMOD | CPTMS | TEA | APTES | Water |
| DMOD 0.75* | 0.75 | 0 | 0 | 0 | q.s. to 100% |
| APTES 1.2 | 0 | 0 | 0 | 1.2 | q.s. to 100% |
| APTES 10 | 0 | 0 | 0 | 10.0 | q.s. to 100% |
| 2030 | 0 | 0 | 0.310 | 9.31 | q.s. to 100% |
| AD51* | 0.5 | 0 | 0 | 1.22 | q.s. to 100% |
| AD101* | 0.5 | 0 | 0 | 2.44 | q.s. to 100% |
| AD201* | 0.5 | 0 | 0 | 4.87 | q.s. to 100% |
| AD501* | 0.5 | 0 | 0 | 12.18 | q.s. to 100% |
| AP** | 0.75 | 0 | 0 | 7.31 | q.s. to 100% |
| APT** | 0.75 | 0 | 0.045 | 7.31 | q.s. to 100% |
| 2015 | 0.75 | 0.12*** | 0.045 | 0 | q.s. to 100% |
| A2015 | 0.75 | 0.12*** | 0.045 | 7.31 | q.s. to 100% |

Notes from Table 1:
*These compositions were prepared by diluting commercially available 42 wt. % DMOD with additional water to a final level of 0.5 or 0.75 wt. % actives as indicated. The 42 wt. % actives DMOD starting material used here was obtained from Millipore Sigma (Product #435694), St. Louis, MO.
**These compositions were prepared by diluting commercially available 5 wt. % DMOD with additional water to a final level of 0.75 wt. % actives with addition of other additives. The 5 wt. % actives DMOD starting material used here was ProShield ® 5000D, EPA Reg. No. 53053-8, obtained from INDUSCO, Inc.
***The amounts of CPTMS in Table 1 indicate wt. % CPTMS purposely added to a composition, ignoring the amount of CPTMS that might be incorporated into a composition from commercially available DMOD. CPTMS can be present in slight amounts in commercially available DMOD as leftover starting material from the $S_N2$ reaction used to synthesize DMOD commercially.

Storage Stability

The compositions in Table 1 were evaluated for storage stability in their neat form. As a measure of storage stability, each aqueous composition was stored at ambient temperature and humidity and periodically evaluated for any stability issues by measuring absorbance at 600 nm in a spectrophotometer over time. Increases in absorbance at 600 nm is a measure of turbidity and an indicator that a composition is failing storage stability over time. It is believed that lack of stability relates to polymerization of the one or more organosilanes into intractable materials that are no longer water soluble, resulting in a measurable turbidity in what was a transparent solution.

FIG. 1 sets forth an x/y plot of absorbance (at 600 nm) versus time for four of the compositions in Table 1, namely AD201, AP, A2015 and APT. Over the course of 4-weeks, it was evident the order of stability for these compositions was A2015>AP≈APT>AD201. The A2015 composition was identified as the best of the four compositions tested in that the composition exhibited essentially no decomposition over a period of 4-weeks.

AD201 serves as control here, without TEA or added CPTMS. Transitioning from formula AD201 to AP represents an increase in both DMOD content and APTES content, resulting in an improvement in storage stability. The transition from AP to APT represents the addition of TEA, which did not seem to improve storage stability (AP≈APT). However, the most striking and unexpected improvement in storage stability came from the addition of 0.12 wt. % CPTMS to the APT composition, i.e., the stability of the A2015 composition. It was interesting to observe that just 0.12 wt. % added CPTMS stabilized the A2015 composition. This is a remarkable result considering DMOD is generally not stable at high pH, which is the situation when APTES is present in the composition. AD201 consists of DMOD in the high pH conditions resulting from APTES. After DMOD hydrolysis, and without CPTMS stabilizer, the DMOD in AD201 is believed to self-polymerize, forming visible precipitate after about 2-weeks.

General Coating Procedures (Laboratory Setting)

In various embodiments, antimicrobial coatings are formed on a surface by applying an aqueous antimicrobial coating composition to the surface, usually by electrostatic spray coating or other spraying method, and then allowing the aqueous antimicrobial coating composition to dry on the surface into a thin film. These antimicrobial thin films are generally invisible.

For testing both durability and residual antimicrobial efficacy of antimicrobial coatings, aqueous antimicrobial coating compositions were applied to 2 inch×2 inch 304 stainless steel carriers. Test carriers were sprayed in a laboratory setting using a robotic slider equipped with an electrostatic sprayer configured to apply the antimicrobial coating composition as a fine mist from a distance of about 3 feet. The misted carriers were then allowed to dry at ambient conditions.

The amount of antimicrobial coating on the test carriers varied by composition. In general, compositions comprising any level of APTES produced dried coatings measuring about 0.50 mg/in$^2$, while compositions not including APTES produced dried coatings measuring about 0.15 mg/in$^2$. The weight per unit area was determined by X-Ray Fluorescence (XRF) spectrometry as explained herein.

The coated carriers were then used in residual antimicrobial efficacy testing and mechanical abrasion testing.

Durability to Abrasion

Testing of prototype compositions also included wear testing, also called abrasion testing or durability. Wear data are indicative of the durability of a coating, and correlate to how well an antimicrobial coating on a surface can withstand frequent handling or other interactions. An existing EPA Protocol may be used to generate the wear data. In certain instances, the EPA protocol may be modified as needed.

EPA Protocol #01-1A, entitled "Protocol for Residual Self-Sanitizing Activity of Dried Chemical Residues on Hard, Non-Porous Surfaces," is a standard test method used for testing the durability or residual efficacy of an antimicrobial coating on a hard surface. The test method utilizes an in-line abrasion machine commonly used in assessing the cleaning ability of detergents. However, instead of a soiled tile being positioned in the machine to be scrubbed by a detergent, carriers as coated per above, having an antimicrobial coating thereon, are positioned in the machine and the antimicrobial coatings "mechanically abraded." The back-and-forth cycling of a weighted scrubber (a weighted "boat" with a cloth or sponge) simulates natural wearing of the antimicrobial coating, such as the wear the coating may experience when frequently handled. In variations of the test protocol, the cloth in the weighted boat may be moistened to simulate the handling of surfaces with a moist hand or a wipe. In various examples, correlations can be made between number of abrasion cycles and frequency of touching an environmental surfaces, e.g., a doorknob. At various wear cycles, carriers may be analyzed by XRF, weighed to determine coating weight loss, and/or inoculated with a test organism to determine residual antimicrobial efficacy for the worn coating.

The abrasion tester suggested in the EPA protocol is a GardCo® Washability and Wear Tester, Model D10V, Cat. No. #WA-2153, available from the Paul N. Gardner Co., Inc., Pompano Beach, Fla., which is the machine used here. Variables in the protocol include the weight of the boat, the material wrapped around the boat (e.g., a cloth wiper), the moisture level, if any, on the wiper, the speed of the back and forth tracking oscillations, and the total number of abrasion cycles, in addition to the composition of the antimicrobial coating on the test carriers and the arrangement of the coated carriers in the machine, (i.e., the tile or grid pattern of the carriers in the machine).

In various embodiments, XRF spectrometry was used to measure the amount of beginning antimicrobial coating and the amount of remaining antimicrobial coating after the coated carriers were subjected to an abrasion protocol. XRF was used to measure the amount of Si atoms, which was then correlated to a weight/unit area of a coating comprising an organosilane. This method is disclosed in U.S. patent application Ser. No. 16/749,343, filed Jan. 22, 2020 and assigned to Allied Bioscience, Inc., the disclosure of which is incorporated herein by reference.

Abrasion Testing Protocol

2"×2" 304 stainless steel carriers were coated with the selected antimicrobial coating composition per the procedure above. The amount of initial coating and the amount of remaining coating after abrasion was determined by XRF. For this purpose, a Bruker Tracer 5i XRF analyzer was used, having a 20 mm$^2$ silicon drift detector with <140 eV @ 250,000 cps Mn Kα resolution for optimum light element analysis. The excitation source was a rhodium thin window X-ray tube and the instrument was equipped with an 8 μm beryllium detector window. The XRF device was equipped with an 8 mm collimator and the applied potential and current were 10 kV and 50 μA, respectively. The measurements were carried out in air atmosphere with a duration of 10 seconds. The Si photon count was assessed in triplicate for each test carrier and the cumulative average was used for all comparisons. The Si photon count data was analyzed with Bruker ARTAX Control XRF software.

A GardCo® Washability machine was used with the weight of the oscillating boat adjusted to 1.0 kg with the necessary auxiliary weights. The weighted boat was equipped with a cotton cloth, and the cloth sprayed at a distance of 75 cm±1 cm with deionized water for 1 second using a Preval™ Sprayer to moisturize the wiper. Abrasion testing was performed immediately after moisturizing the wiper. In the wear protocol, one cycle refers to 2 passes of the weighted boat over the carriers, in a back and forth oscillation. Abrasion speed was set to "2.5," which equated to about 4-6 seconds per each back and forth cycle.

Test carriers were analyzed with the handheld XRF instrument. Using a previously obtained calibration curve, the coating coverage was predicted and plotted against the number of wear cycles.

The results of the durability experiments are shown graphically in FIGS. 2-12.

With reference now to FIGS. 2 and 3, it is evident that DMOD 0.75 (commercially available DMOD diluted with water to 0.75 wt. % actives) and formula 2015, which comprises DMOD, TEA and additional CPTMS added, form thin films having about the same durability, with only about 40-60% of the coating remaining after 30 cycles on the GardCo® Washability machine. In this example, the addition of TEA and additional CPTMS did not improve the durability compared to DMOD 0.75, and may have in fact lessened the durability of the coating.

FIG. 4 shows the durability of a coating obtained from the 2030 composition. Surprisingly, the composition dries into an exceptionally tenacious film. The strong binding of APTES to at least stainless steel suggests that APTES could be used as a way to improve durability of DMOD coatings.

FIGS. 5-8 show the durability curves for thin films obtained from various 0.5 wt. % DMOD antimicrobial coating compositions having progressively increasing amounts of APTES in the coating composition. In progressing from AD51 to AD501, the aqueous antimicrobial coating compositions have 1.22, 2.44, 4.87 and 12.18 wt. % APTES. The reference durability curve for a thin film not including APTES would be the durability curve for DMOD 0.75 composition shown in FIG. 2.

FIG. 5 shows that adding just 1.22 wt. % APTES to a 0.5 wt. % DMOD composition dramatically destroys the durability of the thin film obtained from the composition. The coating resulting from the AD51 coating composition showed worse durability than each of DMOD 0.75 (FIG. 2), 2015 (FIG. 3) and 2030 (FIG. 4), indicating that at an APTES:DMOD ratio of about 5:1, the resulting dried coating either doesn't crosslink well or otherwise doesn't bind to the stainless steel surface properly.

Addition of more APTES eventually improves durability, as seen in FIGS. 6-8. Besides, increasing amounts of APTES was shown to increase storage stability of DMOD compositions. However, including CPTMS would further stabilize the compositions having the same APTES level. APTES is shown to be vital for durability and antimicrobial efficacy of a coating, and CPTMS helps stabilize DMOD in solution at the high pH caused by the presence of APTES.

Bactericidal Suspension Tests—Part 1

As mentioned, various aqueous antimicrobial coating compositions can function as germicidal spray sanitizers and disinfectants. This additional feature may be important if a surface requires an initial sanitization or disinfection by application of a liquid aqueous antimicrobial coating composition, and then that composition is dried into an antimicrobial coating that can keep killing microorganisms that later contact the coating.

The test methodology consisted of a modified version of ASTM-E1052, "Standard Test Method to Assess the Activity of Microbicides Against Viruses in Suspension," but with substitution of gram positive (S. aureus ATCC 6538) and gram negative bacteria (P. aeruginosa ATCC 15442) for the viral test organisms. In the modified test method, 1 part bacterial suspension was mixed with 9 parts test formulation and held at room temperature for 5 minutes.

Summary of the Procedure:

The test bacteria is prepared by growth in liquid culture medium and is subsequently diluted to achieve an inoculum satisfying the requirements of the test method.

0.5 mL of bacterial suspension is added to 4.5 mL of each test composition, briefly vortexed and held at room temperature for 5 minutes. A tube containing 4.5 mL PBS is used as a control.

At the end of the contact time, 1 mL of the test suspension is added to 9 mL D/E neutralizing broth and vortexed for 15 seconds.

Appropriate dilutions of neutralized control and test conditions are made in PBS and plated in duplicate to quantify the number of surviving microorganisms.

The effect of the test composition is determined by comparing the amount of microorganism recovered and calculating the log reduction.

The results of the suspension tests are set forth numerically in Table 2 and also as a bar chart of log reductions in FIG. 12.

TABLE 2

AOAC Suspension Test of Antimicrobial Coating Compositions

| Test Organism | Test Sample | Contact Time | Average CFU/mL | Log Reduction | Percent Reduction |
|---|---|---|---|---|---|
| S. aureus ATCC 6538 | Control PBS | 5 min | 2.24E+06 | N/A | N/A |
| | 2015 | 5 min | 1.90E+03 | 3.07 | 99.915% |
| | 2030 | 5 min | 4.50E+05 | 0.70 | 79.875% |
| | AD51 | 5 min | 5.00E+00 | 5.65 | 99.9998% |
| | AD201 | 5 min | 5.00E+00 | 5.65 | 99.9998% |
| | AP | 5 min | 3.50E+01 | 5.29 | 99.999% |
| | A2015 | 5 min | 1.20E+02 | 4.76 | 99.998% |
| | APT | 5 min | 5.00E+00 | 6.04 | 99.9999% |
| | DMOD 0.75 | 5 min | 1.11E+06 | 0.30 | 50.447% |
| | APTES 10 | 5 min | 6.00E+05 | 0.57 | 73.166% |
| | APTES 1.2 | 5 min | 7.64E+05 | 0.47 | 65.832% |

From the data in Table 2 and FIG. 12, it was evident that 2030, DMOD 0.75, APTES 10 and APTES 1.2 did not perform well at all against S. aureus in the suspension tests. However, when DMOD and TEA were combined (e.g., compositions 2015, AD51 and AD201), the solution antimicrobial efficacy increased dramatically, indicating an unexpected synergistic effect in the combination of DMOD, APTES and TEA.

Surface-Time Kill Study of Various Antimicrobial Coatings

Seven of the compositions from Table 1 were applied to stainless steel carriers, dried into antimicrobial coatings, and the coated carriers tested for residual antimicrobial activity against several organisms, namely K. aerogenes ATCC 13048, P. aeruginosa ATCC 15442, and S. aureus ATCC 6538.

The test methodology consisted of a modified version of ASTM-E1153, "Test Method for Efficacy of Sanitizers Recommended for Inanimate Non-Food Contact Surfaces." The standard method was modified to directly assess the efficacy of the continuously active antimicrobial coatings. In this test, the organisms are inoculated on the coating and efficacy is evaluated after a 2-hour contact time.

Summary of the Procedure:

The test bacteria is prepared by growth in liquid culture medium and is subsequently diluted to achieve an inoculum that satisfies the requirements of the test method.

0.01 mL of bacterial suspension is inoculated onto the coated stainless steel carriers at ambient temperature and then transferred to a 25° C. incubator with constant humidity for the remainder of the 2-hour contact time.

At the conclusion of 2-hours, test carriers are fully emerged in neutralizer broth, briefly sonicated and agitated on an orbital shaker to release any surviving microorganisms from the carrier.

Appropriate dilutions of neutralized control and test carriers are made in PBS and plated in duplicate to quantify the number of surviving microorganisms.

The effect to the coating is determined by comparing the level of microorganisms recovered and calculating the log reduction.

Table 3 sets forth the results of the modified E1153 surface-time kill study for coatings obtained from the aqueous antimicrobial coating compositions AD51, AD101, AD201, AD501, AP, APT, and A2015. None of the coated carriers were subjected to abrasion, and were tested for residual antimicrobial efficacy as coated (i.e., the carriers were "fresh"). These results are also presented in FIG. 13 as a bar graph of the observed log reductions.

TABLE 3

Modified E1153 Surface-Time Kill Study

| Test Organism | Contact Time | Log₁₀ Reduction | | | | | | |
|---|---|---|---|---|---|---|---|---|
| | | AD51 | AD101 | AD201 | AD501 | AP | APT | A2015 |
| K. aerogenes ATCC 13048 | 2 hours | 2.24 | 2.92 | 2.29 | 2.56 | 5.10 | 4.84 | 5.27 |
| P. aeruginosa ATCC 15442 | | 1.40 | 2.99 | 1.89 | 2.94 | 3.73 | 4.15 | 3.17 |
| S. aureus ATCC 6538 | | <2.00 | 2.89 | 2.90 | 3.21 | 4.21 | 5.26 | 4.24 |

From the data presented in Table 3 and FIG. 13, it was evident that against *S. aureus*, increasing APTES levels (from AD51 through AD501) increased residual antimicrobial efficacy. However, for the other two organisms, *K. aerogenes* ATCC 13048 and *P. aeruginosa* ATCC 15442, the results varied between AD51, AD101, AD201 and AD501 coatings, with no trends identified.

Comparing AP and APT, the data also demonstrated the benefit of added triethanolamine against gram-negative bacteria. Although the data may show a slight reduction in residual antimicrobial efficacy when adding CPTMS, there is a very large improvement in storage stability of DMOD/APTES compositions if CPTMS is added, as discussed previously.

Surface-Time Kill Study of Various Antimicrobial Coatings—Fresh Versus Worn Carriers The residual antimicrobial efficacy testing was extended to both fresh coated carriers and coatings previously subjected to an abrasion protocol. The coating procedure, the abrasion protocol using the GardCo® Washability and Wear Tester, and the modified ASTM E1153 method have been described.

The test organisms for the residual antimicrobial efficacy testing on both fresh and worn coated carriers was *S. aureus* ATCC 6538 (results in Table 4A and presented as bar graphs of log reductions in FIG. 14A) and *P. aeruginosa* ATCC 15442 (results in Table 4B and presented as bar graphs of log reductions in FIG. 14B).

TABLE 4A

Modified E1153 Surface-Time Kill Study on Fresh and Worn Coatings Inoculated with *S. aureus* ATCC 6538

| Test Organism | Test Sample | Carrier Condition | Contact Time | Geo Mean CFU/carrier | Log Reduction | Percent Reduction |
|---|---|---|---|---|---|---|
| S. aureus ATCC 6538 | Control | N/A | 0 | 3.50E+06 | N/A | N/A |
| | Control | N/A | 2 hours | 1.59E+06 | 0.34 | N/A |
| | Commercial DMOD | Fresh | 2 hours | 2.66E+05 | 0.78 | 83.295% |
| | Commercial DMOD | Worn | 2 hours | 2.26E+05 | 0.85 | 85.776% |
| | 2015 | Fresh | 2 hours | 2.69E+05 | 0.77 | 83.071% |
| | 2015 | Worn | 2 hours | 1.98E+05 | 0.91 | 87.565% |
| | 2030 | Fresh | 2 hours | 8.11E+04 | 1.29 | 94.899% |
| | 2030 | Worn | 2 hours | 7.69E+04 | 1.32 | 95.164% |
| | A2015 | Fresh | 2 hours | 9.22E+01 | 4.24 | 99.994% |
| | A2015 | Worn | 2 hours | 3.79E+02 | 3.62 | 99.976% |
| | AP | Fresh | 2 hours | 9.72E+01 | 4.21 | 99.994% |
| | AP | Worn | 2 hours | 5.81E+01 | 4.44 | 99.996% |
| | AD201 | Fresh | 2 hours | 1.87E+02 | 3.93 | 99.988% |
| | AD201 | Worn | 2 hours | 1.17E+03 | 3.13 | 99.926% |
| | APT | Fresh | 2 hours | 8.66E+00 | 5.26 | 99.999% |
| | APT | Worn | 2 hours | 5.36E+01 | 4.47 | 99.997% |

TABLE 4B

Modified E1153 Surface-Time Kill Test on Fresh and Worn Coatings Inoculated with *P. aeruginosa* ATCC 15442

| Test Organism | Test Sample | Carrier Condition | Contact Time | Geo Mean CFU/carrier | Log Reduction | Percent Reduction |
|---|---|---|---|---|---|---|
| P. aeruginosa ATCC 15442 | Control | N/A | 0 | 1.72E+06 | N/A | N/A |
| | Control | N/A | 2 hours | 5.71E+05 | 0.48 | N/A |
| | 2015 | Fresh | 2 hours | 3.34E+05 | 0.23 | 41.547% |
| | 2015 | Worn | 2 hours | 2.14E+05 | 0.43 | 62.545% |
| | 2030 | Fresh | 2 hours | 4.20E+01 | 4.13 | 99.993% |
| | 2030 | Worn | 2 hours | 1.65E+03 | 2.54 | 99.711% |
| | A2015 | Fresh | 2 hours | 1.46E+02 | 3.59 | 99.974% |
| | A2015 | Worn | 2 hours | 1.67E+02 | 3.53 | 99.971% |
| | APT | Fresh | 2 hours | 1.60E+01 | 4.55 | 99.997% |
| | APT | Worn | 2 hours | 3.23E+01 | 4.25 | 99.994% |

As seen in Table 4A and FIG. 14A, antimicrobial coatings obtained from compositions AP, APT, A2015 and AD201 were effective against *S. aureus* inoculation, with A2015 and APT coatings more effective against the inoculum than the 2015 coating. Also, as seen in Table 4B and FIG. 141B, A2015 and APT coatings were more effective than the 2015 coating against *P. aeruginosa* inoculation. APTES and TEA showed an unexpected synergistic effect in DMOD-based compositions with regards to solution efficacy, coating efficacy, as well as coating durability.

General Coating Procedures (Residential, Institutional and Industrial Settings)

In various embodiments of the present disclosure, aqueous antimicrobial coating compositions described herein are used in the "real world" for coating numerous environmental surfaces found in homes, institutions, schools, public transportation, and industries, thus providing residual antimicrobial efficacy to the surface. In addition to coating household surfaces, it is desirable to coat surfaces found in public places, and in particular, those surfaces in public places that are frequently touched by human contact or prone to contamination from spillage, sneezing, nasal discharge, and other unsanitary behaviors. In various embodiments, coatings formed on surfaces from the aqueous antimicrobial coating compositions herein are durable for a time sufficient to mitigate transmission of microbes via the coated surface. For example, coating various surfaces in hospitals, such as chair arms, tables, countertops at reception and nursing stations, doorknobs, IV poles, carts, trays, etc., can mitigate hospital acquired infections in the hospital. Further, coating frequently touched surfaces found in public transportation, such as surfaces in the interiors of busses, subway cars, train cars, and airplanes, and in schools, universities, fitness centers, bars, taverns and the like, can reduce the spread of pathogens in those locations. Coating frequently touched surfaces in public transportation, schools, institutions and various businesses, can mitigate the spread of infectious diseases such as the seasonal flu virus or other pathogens having transmission through touch (e.g., contaminated surface to eye or nostril). Of particular interest is the coating of surfaces found in a passenger airplane, including, but not limited to, overhead bid latches and lids, fold-down tray tables, headrests, armrests, seatbelts, seatbelt buckles, bathroom door latches, toilet seats, sinks, faucet handles, and tissue dispensers.

In general, aqueous antimicrobial coating compositions of the present disclosure may be applying to a surface by spray application, dip-coating or wiping from a wetted cloth.

Methods for applying the aqueous coating compositions of the present disclosure onto surfaces may vary for a number of reasons, such as the size of the surface, location of the surface, if the surface is movable, and the nature of the area surrounding the surface to be coated, amongst other considerations. For example, a procedure for fogging the interior of a subway car with a spray mist may be quite different than a procedure used for coating the surface of a tray table in a passenger airplane or the doorknobs in a residential home, which may be from a more targeted spray or a wetted cloth. The surfaces of various objects may be all coated at the same time, such as fogging the inside of a subway car, or various surfaces may be coated one surface at a time, such as coating an airplane tray table, or a student's desk in a grade school, or a refrigerator handle in a breakroom at a company.

In various embodiments, spray application of aqueous coating compositions of the present disclosure onto surfaces may be targeted or random. Factors influencing targeted versus random coating include consideration of the number and complexity of the surfaces to be coated, the time required and the cost. For example, it is likely more cost effective to randomly fog the inside of a subway car than to individually spray coat each of the handrails, seatback frames, etc. individually. Targeted spray application may comprise narrow spray patterns and/or lower pressures, whereas random spray application may comprise wide spray patterns and/or higher pressures. In either instance, electrostatic spraying may be used, in that electrostatic methods may convey spray particles randomly as a fog or may channel spray particles to a particular surface depending on the nature of the grounding. Further, targeted spray application may utilize familiar packaging like trigger spray bottles and aerosol cans.

In various embodiments, aqueous coating compositions of the present disclosure may be applied to various surfaces by dip-coating, such as if the object is very small, or if the object to be coated is part of an industrial process where replicates of the same object are coated, such as in an assembly line. Certain objects may be dip-coated, allowed to dry or manually dried, and then hygienically packaged for later use. In various embodiments, surfaces may be wiped with an aqueous antimicrobial coating composition. For wiping, a cloth or paper towel may be wetted with the aqueous antimicrobial coating composition and the surface wiped with the wetted toweling.

1. Spray Application on Environmental Surfaces

In various embodiments, the aqueous coating compositions of the present disclosure may be applied to various surfaces by any one of manual spraying, compressed air spraying, electrostatic spraying, and aerosol spraying. Other spray application methods may be envisioned, and this list is not meant to be exhaustive.

Depending on the size of the surfaces on the various objects to be coated, along with other considerations such as cost, time commitment, persons and other surfaces in the vicinity of the surfaces to be coated, the portability of the objects to be coated, and the number and variation of the surfaces to be coated, spray application may comprise a distance of 0 inches to at least about 50 feet or more between a particular spray nozzle outlet and the surface to be spray coated with an aqueous antimicrobial coating composition. This range in distance of spray application can be achieved, at least in part, by choice of spray method, nozzle configuration, and spray pressure. For coating at really close distances, such as less than 1 inch, critical spraying can be employed such as through a laboratory Preval™ Sprayer, or by using a wetted towel instead of a sprayer. Long range spray coating is important when, for example, fogging the inside of a subway car where the distances between the sprayer and the far corners of the interior of the subway car could be 25-50 feet or more.

In various embodiments, and depending on the particular aqueous antimicrobial coating composition used, the type of spraying, and other considerations, the antimicrobial coating on a surface may weigh from about 1 $\mu g/cm^2$ up to about 500 $mg/cm^2$ of surface, after the coated surfaces are allowed to dry at ambient or dried with applied heat/air.

In any one of manual spraying, compressed air spraying, electrostatic spraying, and aerosol spraying herein, the aqueous antimicrobial coating composition will be expelled from some type of spray nozzle. A spray nozzle herein may deliver a spray, a jet, a mist, a stream, or a foam.

A spray nozzle herein may deliver any suitable spray pattern, such as conical, flat vertical, flat horizontal. A spray pattern for use herein may be conical, with a cone of about 5° to about 120°.

Each of manual, compressed air and electrostatic spraying can include a bottle, canister or tank, or any suitable vessel to hold sufficient quantity of aqueous antimicrobial coating product to be applied to a surface. For example, residential application may employ manual trigger sprayers having spray bottles of less than about 1 liter (34 ounces) in volume, or aerosol spray cans typically having about 473 mL (16 ounces) volume.

Manual trigger spraying may be from any of the common packaging used in the consumer cleaning market. For example, bottles and pump sprayers may be obtained from Afa Dispensing, Helmond, The Netherlands. Sprayers may comprise conventional trigger sprayers or pre-compression trigger sprayers. A typical trigger sprayer for use herein may be polypropylene, with a 28-400 neck finish and a 9.25 inch dip tube, which would fit a 32 oz. natural HDPE plastic (25% PCR resin) trigger sprayer bottle, 28 mm, with a 28-400 neck finish. The spray pattern can be chosen as desired. Trigger spray application of an aqueous antimicrobial coating composition herein may comprise a distance of from about 1 inch to about 5 feet between the trigger sprayer and the surface to be coated. A trigger sprayer for dispensing an aqueous antimicrobial coating composition may deliver from about 0.5 mL to about 2.0 mL per trigger. Trigger sprayers may also be automated wherein a small battery in the sprayer shroud operates the sprayer so that the user does not need to repeatedly "pump" the trigger sprayer.

In other versions of manual spraying, a tank may be pressurized by pumping a hand pump. For compressed air spraying, an air compressor pressurizes a handheld spray gun, which comprises a canister filled with the composition to be sprayed.

In electrostatic spraying, the configuration of the equipment is very much like compressed air spraying except that an electrical connection is made to the spray head. Aerosol application comprises the familiar aerosol can one sees around the house for everything from air fresheners to hobby paints.

For aerosol application, an aqueous antimicrobial coating composition in accordance with the present disclosure is aerosolized in an aerosol package that includes a can, a valve, an actuator, a propellant, and optionally, various corrosion inhibitors depending on the type of can. Aerosol application of an aqueous antimicrobial coating composition is similar to painting from an aerosolized can of paint.

A. Storage and Dispensing Tank

In various embodiments, a spray application comprises one, two, three, four or more tanks, each suitable for liquid storage and, in particular, for the storage of one or more aqueous antimicrobial coating compositions. A tank herein may be fashioned of any suitable material that is able to contain liquids and that is chemically compatible with the aqueous antimicrobial coating compositions contained therein, such as plastic, glass, or metal, and may further comprise a removable closure for refilling purposes. In various embodiments, a tank may comprise a bag-in-a-box package, or a standard pail with a bung that can be tapped. In other examples, a tank herein may comprise an aerosol package further comprising a liquid and an aerosol propellant (discussed in more detail herein). A tank may be of any capacity, such as for example, from about 0.5 liter capacity up to about 40 liter. The capacity of a tank may depend on a number of considerations, such as, how many tanks are to be used, the nature of the liquid materials in the tank, (e.g. as relating to the amount of material typically sprayed on a surface), whether the tank is refillable or not refillable and disposable, and how portable the spray apparatus needs to be, amongst other considerations. For example, one 30 liter tank may be used, whereas in other embodiments, three 10 liter tanks may be used. In another example, four, five or six, or more, 500 mL disposable aerosol cans may be employed to apply an aqueous antimicrobial coating herein.

B. Sprayer

In various embodiments, the sprayer comprises all the spray components necessary for any one of manual spraying, compressed air spraying, electrostatic spraying, or aerosol spraying of the aqueous antimicrobial coating composition residing in a container. Exemplary sprayers herein minimally comprise a chemical delivery hose suitable for liquid flow and a spray gun in fluid communication with the tank. In various embodiments, portions of the sprayer are extendable away from the tank, such as to allow for spraying of surfaces that are several feet or yards away from the tank. Thus, in several embodiments, either or both of a compressed air supply line and a chemical delivery hose can be disposed on a retractable hose reel such that either or both can be pulled out when needed and retracted back when not needed. The length of these two lines can be any length, such as from just a foot or so up to several hundred feet. Depending on the desired mode of spraying enabled by the sprayer, only a chemical delivery hose may be connected to a spray gun. In other examples, both a chemical delivery hose and a compressed air supply line may be connected to a spray gun. In general, an electrostatic spray gun, although including both of these, does not require a third line to the spray gun, i.e. an electrical cable, because an electrostatic spray gun generally comprises an internal turbine operated by the compressed air, and this turbine produces the electricity supplied to the electrode needle of the spray gun.

Regardless of what type of spraying the sprayer comprises, any number and type of sensors and switches, weight sensors, liquid level floats, optical sensors, and the like, may be employed to enable recordation of spray times and/or the amount of aqueous antimicrobial coating composition dispensed from a container during a spraying session. These data can be used to calculate a weight of coating application in $mg/cm^2$ or any other suitable units.

Spray nozzles may deliver any necessary droplet size and spray pattern as needed for the coating of particular surfaces with the aqueous antimicrobial coating compositions of the present disclosure. Spray nozzles may be metal or plastic or combinations of materials.

All the components that may enable each of these modes of spraying are available, for example, from Finishing Consultants, Inc., Everett, Wash., amongst other suppliers.

Manual Spraying

In various embodiments, the sprayer for manual spraying comprises a fluidic pump that moves chemicals from one or more tanks through a chemical delivery hose and out to a spray gun. The pump may comprise any type of in-line fluid pump that can supply the liquid to be sprayed at a suitable pressure such that the liquid is aerosolized by the spray nozzle on the spray gun. In various embodiments, a sprayer comprises two sections of chemical delivery hose with connectors at each end of both sections, a spray gun, and an in-line pump disposed anywhere between the spray gun and the tank, wherein one section of hose fluidically connects a tank to the inlet of the fluid pump and the other section of hose fluidically connects the outlet of the fluid pump to the spray gun. The connectors may be of any type, such as for example, quick disconnect Swage-type fittings, or threaded connectors, or any other type of connectors for fastening hose to a hose bib. The chemical delivery hose may comprise any material that is reasonably flexible, such as plastic, and may comprise combinations of materials. For example, a chemical delivery hose herein may comprise a polyethylene tube surrounded by a stainless steel or other type of metal mesh for reinforcement. In this way, the metal mesh protects and reinforces the inner polyethylene tubing, extending its life. Other tubing can be selected depending on the corrosive nature of the chemicals to be sprayed, and include for example, polycarbonate and Teflon. The inside diameter of a chemical delivery hose herein is from about 0.25 inches up to about 2 inches.

The spray gun of the sprayer for manual spraying further comprises a handle that actuates the spray nozzle by opening a fluid passageway between the chemical delivery hose and the spray nozzle. The handle may further comprise a sensor that detects when the handle is gripped or actuated and when then handle is released. In this way, a sensor disposed on the spray handle of the spray gun detects the length of time the spray gun is spraying. Data from the spray gun sensor can be used to calculate the amount of aqueous antimicrobial coating composition sprayed on a surface.

Compressed Air Spraying

In various embodiments of compressed air spraying, the sprayer may comprise a chemical delivery hose enabling fluid communication between a tank and a spray gun as per the manual spraying option. In various aspects, compressed air spraying is equivalent to commercial liquid spraying seen in the painting and finishing industry wherein the tank of liquid is pressurized rather than pumped out. In compressed air spraying, pressure in the tank of liquid forces liquid from the tank through a delivery hose to the spray gun where it is atomized by the spray nozzle. In various embodiments, the sprayer further comprises an air compressor that pressurizes a tank. A pressurized tank for liquid spraying is sometimes referred to as a "pressure pot." The air compressor may cycle on and off as necessary to maintain a constant pressure in the tank, such as up to about 100 psi. The air compressor may switch on automatically after a period of spraying that acted to reduce the pressure in the tank below a certain threshold pressure.

In other examples, a small reservoir or "cup" may be disposed on the spray gun, which can in various embodiments replace the need for a tank altogether, or that can supplement the contents of a container with additional chemicals. A spray gun having a small cup such as having about a 0.5 L to about a 2 L capacity is somewhat analogous to commercial paint sprayers used in auto collision shops and other smaller scale spray operations.

As per manual spraying with a similar or identical spray gun, the spray gun of the sprayer may further comprise a handle that actuates the spray nozzle by opening a fluid passage between the delivery hose and the spray nozzle. The handle may further comprise a sensor that detects when the handle is actuated and when then handle is released. In this way, the sensor on the spray handle of the spray gun detects the length of time the spray gun is spraying chemicals.

Electrostatic Spraying

In various embodiments, the sprayer comprises an electrostatic spray system. Electrostatic spraying comprises positively charging the atomized liquid as it leaves the spray gun such that the atomized particles are attracted to a surface that is electrically grounded. Electrostatic spraying in institutional, industrial and public transportation settings is promoted by the fact that many objects to be coated are grounded, and that many frequently touched surfaces of interest may be made mostly or entirely of metal. A spray gun suitable for electrostatic spraying may be manual or automatic electrostatic spray or low pressure or high pressure air-assisted electrostatic spray guns. For the sprayer herein, an electrostatic spray gun comprises two connections, one comprising the chemical delivery hose and the other comprising the compressed air supply line. The liquid chemicals to be sprayed may be supplied to the electrostatic spray gun by manual pumping (an in-line fluid pump) or from a pressurized tank.

In various embodiments, a sprayer for electrostatic spraying comprises two sections of chemical delivery hose with connectors at each end of both sections, an electrostatic spray gun, an in-line pump disposed anywhere between the spray gun and the tank, wherein one section of hose fluidically connects a container to the inlet of the fluid pump and the other section of hose fluidically connects the outlet of the fluid pump to the spray gun, an air compressor, and a compressed air supply line with connectors at each end for providing compressed air from the compressor to the air inlet of the electrostatic spray gun. The sprayer may further comprise two hose reels, one for retracting and managing the chemical supply hose and the other for retracting and managing the compressed air supply line.

In various embodiments, a sprayer for electrostatic spraying comprises one section of chemical delivery hose with connectors at each end, an electrostatic spray gun, wherein the one section of hose fluidically connects a tank to the electrostatic spray gun, an air compressor to pressurize a tank, and a compressed air supply line with connectors at each end to bring compressed air from the air compressor to the air inlet of the electrostatic spray gun. The sprayer may further comprise two hose reels, one for retracting and managing the chemical supply hose and the other for retracting and managing the compressed air supply line.

Aerosol Spraying

In various embodiments, one or more aqueous antimicrobial coating compositions may be provided in an aerosol package. Aerosol packaging comprises a liquid composition intimately mixed with a propellant and sealed in a can, usually metal, which is equipped with an actuatable valve. Another type of aerosol package comprises a "bag-in-can" concept wherein the liquid composition is in a bag and the propellant is in the can but outside the bag. An aerosol valve typically comprises a dip tube, a valve cup and a valve stem. Pressing down on the stem, or moving it laterally, causes the valve stem to open, whereby the pressurized mixture of liquid plus propellant is propelled up the dip tube and out the bore through the valve stem. Usually an aerosol package includes a button actuator that sits atop the valve stem, and which includes a nozzle insert that atomizes the liquid coming through the stem.

Additional Aspects

In various embodiments of the present disclosure, a method of forming an aqueous antimicrobial coating composition is described. The method comprises mixing each of at least two organosilanes in water to form an aqueous antimicrobial coating composition.

In various embodiments, each of the at least two organosilanes in the method of forming an antimicrobial coating composition have a structure, $R—Si(OR')_3$, wherein:

$R=—(CH_2)_3—Y$;

$Y={}^{+}—N(CH_3)_2(C_{18}H_{37})X^-$; ${}^{+}—N(CH_3)_2(C_{14}H_{29})X^-$; ${}^{+}—N(C_{10}H_{21})_2(CH_3)X^-$; —Cl or —$NH_2$;

$X^-$=halide, sulfate, nitrate, phosphate, carbonate, organic sulfonate, organic carbonate, $BF_4^-$, or $ClO_4^-$; and R'=H, methyl or ethyl, or a $C_3$-$C_6$ straight-chained, branched or cyclic alkyl group with the proviso that the organosilane R—Si(OR')$_3$ having the $C_3$-$C_6$ straight-chained, branched or cyclic alkyl group hydrolyzes in the aqueous antimicrobial coating composition to R—Si(OH)$_3$.

In various embodiments, the method of forming an aqueous antimicrobial coating composition further comprises mixing at least one organic amine with the water. In various embodiments, at least one organic amine fits the structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

In various embodiments, a method of forming an aqueous antimicrobial coating composition comprises mixing from about 0.1 wt. % to about 1.0 wt. % DMOD; and from 0 wt. % to about 1.0 wt. % TEA in water.

In various embodiments, a method of forming an aqueous antimicrobial coating composition comprises mixing from about 1.0 wt. % to about 15.0 wt. % APTES; and from 0 wt. % to about 1.0 wt. % TEA in water.

In various embodiments, a method of forming an aqueous antimicrobial coating composition comprises mixing from about 0.1 wt. % to about 1.0 wt. % DMOD; from about 1.0 wt. % to about 15.0 wt. % APTES; and from 0 wt. % to about 1.0 wt. % TEA in water.

In various embodiments, a method of forming an aqueous antimicrobial coating composition comprises mixing from about 0.1 wt. % to about 1.0 wt. % DMOD; from about 0.01 wt. % to about 0.5 wt. % CPTMS; and from 0 wt. % to about 1.0 wt. % TEA in water.

In various embodiments, a method of forming an aqueous antimicrobial coating composition comprises mixing from about 0.1 wt. % to about 1.0 wt. % DMOD; from about 0.01 wt. % to about 0.5 wt. % CPTMS; from about 1.0 wt. % to about 15.0 wt. % APTES; and from 0 wt. % to about 1.0 wt. % TEA in water.

In various embodiments of the present disclosure, a method of forming an antimicrobial coating on a surface is described.

In various embodiments, a method of forming an antimicrobial coating on a surface comprises, for example:

(a) applying an aqueous antimicrobial coating composition to the surface, the aqueous antimicrobial coating composition comprising a mixture of at least two organosilanes, each of the at least two organosilanes having a structure, R—Si(OR')$_3$, wherein:
R=—(CH$_2$)$_3$—Y;
Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;
$X^-$=halide, sulfate, nitrate, phosphate, carbonate, organic sulfonate, organic carbonate, $BF_4^-$, or $ClO_4^-$; and
R'=H, methyl or ethyl, or a $C_3$-$C_6$ straight-chained, branched or cyclic alkyl group with the proviso that the organosilane R—Si(OR')$_3$ having the $C_3$-$C_6$ straight-chained, branched or cyclic alkyl group hydrolyzes in the aqueous antimicrobial coating composition to R—Si(OH)$_3$; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the aqueous antimicrobial coating composition further comprises at least one organic amine having the structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, a method of forming an antimicrobial coating on a surface comprises, for example:

(a) applying an aqueous antimicrobial coating composition to the surface, the aqueous antimicrobial coating composition comprising a mixture of from about 0.1 wt. % to about 1.0 wt. % DMOD and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, a method of forming an antimicrobial coating on a surface comprises, for example:

(a) applying an aqueous antimicrobial coating composition to the surface, the aqueous antimicrobial coating composition comprising a mixture of from about 1.0 wt. % to about 15.0 wt. % APTES and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, a method of forming an antimicrobial coating on a surface comprises, for example:

(a) applying an aqueous antimicrobial coating composition to the surface, the aqueous antimicrobial coating composition comprising a mixture of from about 0.1 wt. % to about 1.0 wt. % DMOD; from about 1.0 wt. % to about 15.0 wt. % APTES; and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, a method of forming an antimicrobial coating on a surface comprises, for example:

(a) applying an aqueous antimicrobial coating composition to the surface, the aqueous antimicrobial coating composition comprising a mixture of from about 0.1 wt. % to about 1.0 wt. % DMOD; from about 0.01 wt. % to about 0.5 wt. % CPTMS; and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, a method of forming an antimicrobial coating on a surface comprises, for example:

(a) applying an aqueous antimicrobial coating composition to the surface, the aqueous antimicrobial coating composition comprising a mixture of from about 0.1 wt. % to about 1.0 wt. % DMOD; from about 0.01 wt. % to about 0.5 wt. % CPTMS; from about 1.0 wt. % to about 15.0 wt. % APTES; and from 0 wt. % to about 1.0 wt. % TEA in water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.5 wt. % DMOD; 1.22 wt. % APTES; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.5 wt. % DMOD; 2.44 wt. % APTES; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.5 wt. % DMOD; 4.87 wt. % APTES; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.5 wt. % DMOD; 12.18 wt. % APTES; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.75 wt. % DMOD; 7.31 wt. % APTES; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.75 wt. % DMOD; 7.31 wt. % APTES; 0.045 wt. % TEA; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.75 wt. % DMOD; 0.12 wt. % CPTMS; and 0.045 wt. % TEA; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.75 wt. % DMOD; 0.12 wt. % CPTMS; 7.31 wt. % APTES; 0.045 wt. % TEA; remainder water; and (b) allowing the aqueous antimicrobial coating composition to dry under ambient conditions, or drying the aqueous antimicrobial coating composition under heated conditions, to form the antimicrobial coating on the surface. In various embodiments, the applying comprises electrostatic spray application of the aqueous antimicrobial coating composition onto the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

A method of forming an antimicrobial coating on a surface comprises, for example:

(a) applying an aqueous antimicrobial coating composition to the surface, the aqueous antimicrobial coating composition consisting essentially of 0.75 wt. % DMOD; 0.27 wt. % CPTMS; 7.31 wt. % APTES; 0.045 wt. % TEA; remainder water; and (b) allowing the aqueous antimicrobial coating composition to dry under ambient conditions, or drying the aqueous antimicrobial coating composition under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, 0.15 wt. % of the CPTMS is from the commercial source of the DMOD, whereas 0.12 wt. % is additional CPTMS added to the aqueous antimicrobial coating composition.

In further aspects, an antimicrobial coating on a surface is characterized by a method of forming it on the surface, as follows:

An antimicrobial coating on a surface formed by a method comprising, for example:

(a) applying an aqueous antimicrobial coating composition to the surface, the aqueous antimicrobial coating composition comprising a mixture of at least two organosilanes, each of the at least two organosilanes having a structure, R—Si(OR')$_3$, wherein:
R=—(CH$_2$)$_3$—Y;
Y=$^+$—N(CH$_3$)$_2$(C$_{18}$H$_{37}$)X$^-$; $^+$—N(CH$_3$)$_2$(C$_{14}$H$_{29}$)X$^-$; $^+$—N(C$_{10}$H$_{21}$)$_2$(CH$_3$)X$^-$; —Cl or —NH$_2$;
X$^-$=halide, sulfate, nitrate, phosphate, carbonate, organic sulfonate, organic carbonate, BF$_4^-$, or ClO$_4^-$; and
R'=H, methyl or ethyl, or a C$_3$-C$_6$ straight-chained, branched or cyclic alkyl group with the proviso that the organosilane R—Si(OR')$_3$ having the C$_3$-C$_6$ straight-chained, branched or cyclic alkyl group hydrolyzes in the aqueous antimicrobial coating composition to R—Si(OH)$_3$; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the aqueous antimicrobial coating composition further comprises at least one organic amine having the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various embodiments, the at least one organic amine comprises TEA.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to a surface, the aqueous antimicrobial coating composition comprising a mixture of from about 0.1 wt. % to about 1.0 wt. % DMOD and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition comprising a mixture of from about 1.0 wt. % to about 15.0 wt. % APTES and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition comprising a mixture of from about 0.1 wt. % to about 1.0 wt. % DMOD; from about 1.0 wt. % to about 15.0 wt. % APTES; and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition comprising a mixture of from about 0.1 wt. % to about 1.0 wt. % DMOD; from about 0.01 wt. % to about 0.5 wt. % CPTMS; and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition comprising a mixture of from about 0.1 wt. % to about 1.0 wt. % DMOD; from about 0.01 wt. % to about 0.5 wt. % CPTMS; from about 1.0 wt. % to about 15.0 wt. % APTES; and from 0 wt. % to about 1.0 wt. % TEA in water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.5 wt. % DMOD; 1.22 wt. % APTES; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.5 wt. % DMOD; 2.44 wt. % APTES; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.5 wt. % DMOD; 4.87 wt. % APTES; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.5 wt. % DMOD; 12.18 wt. % APTES; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.75 wt. % DMOD; 7.31 wt. % APTES; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.75 wt. % DMOD; 7.31 wt. % APTES; 0.045 wt. % TEA; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.75 wt. % DMOD; 0.12 wt. % CPTMS; and 0.045 wt. % TEA; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.75 wt. % DMOD; 0.12 wt. % CPTMS; 7.31 wt. % APTES; 0.045 wt. % TEA; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

An antimicrobial coating formed by a method comprising, for example:

(a) applying an aqueous antimicrobial coating composition to the surface, the aqueous antimicrobial coating composition consisting essentially of 0.75 wt. % DMOD; 0.27 wt. % CPTMS; 7.31 wt. % APTES; 0.045 wt. % TEA; remainder water; and (b) allowing the aqueous antimicrobial coating composition to dry on the surface under ambient conditions, or drying the aqueous antimicrobial coating composition on the surface under heated conditions, to form the antimicrobial coating on the surface.

In various embodiments, the step of applying comprises spray coating the aqueous antimicrobial coating composition on the surface. In various embodiments, the spray coating further comprises electrostatic spraying. In various embodiments, the aqueous antimicrobial coating composition is allowed to dry under ambient conditions.

In various embodiments, 0.15 wt. % of the CPTMS is from the commercial source of the DMOD, whereas 0.12 wt. % is additional CPTMS added to the aqueous antimicrobial coating composition.

In various embodiments, a method of stabilizing a high pH aqueous antimicrobial coating composition comprising DMOD and APTES in water comprises adding CPTMS to the aqueous antimicrobial coating composition.

A method of stabilizing a high pH aqueous antimicrobial coating composition comprising from about 0.1 wt. % to about 1.0 wt. % DMOD; from about 1.0 wt. % to about 15.0 wt. % APTES; and from 0 wt. % to about 1.0 wt. % TEA in water comprises, for example: adding from about 0.01 wt. % to about 0.5 wt. % CPTMS to the aqueous coating composition.

While the various embodiments have been illustrated in detail, it should be apparent that modifications and adaptations to those embodiments may occur to one skilled in the art without departing from the scope as set forth herein.

Antimicrobial coating compositions capable of forming antimicrobial coatings on surfaces, methods of applying antimicrobial coating compositions to surfaces, and antimicrobial coatings therefrom are provided. When a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in various embodiments.

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. An aqueous antimicrobial coating composition comprising:
   (a) a mixture from about 0.1 wt. % to about 1.0 wt. % of dimethyloctadecyl[3-(trihydroxysilyl)propyl]ammonium chloride (DMOD), 3-chloropropyltrimethoxysilane (CPTMS) and from about 2.5 wt. % to about 12.5 wt. % 3-aminopropyltriethoxysilane (APTES) in water; and
   (b) optionally, at least one organic amine having a structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12,
   wherein the aqueous antimicrobial coating composition exhibits an absorbance at 600 nm of less than about 0.2 after 4-weeks of ambient storage.

2. The aqueous antimicrobial coating composition of claim 1, wherein the at least one organic amine is present at from about 0.01 wt. % to about 1.0 wt. %, based on the total weight of the aqueous antimicrobial coating composition.

3. The aqueous antimicrobial coating composition of claim 1, wherein the at least one organic amine comprises triethanolamine.

4. The aqueous antimicrobial coating composition of claim 1, comprising 0.045 wt. % triethanolamine.

5. The aqueous antimicrobial coating composition of claim 1, comprising from about 0.01 wt. % to about 0.5 wt. % 3-chloropropyltrimethoxysilane.

6. The aqueous antimicrobial coating composition of claim 1, comprising 0.5 wt. % dimethyloctadecyl[3-(trihydroxysilyl)propyl]ammonium chloride.

7. The aqueous antimicrobial coating composition of claim 1, comprising 0.75 wt. % dimethyloctadecyl[3-(trihydroxysilyl)propyl]ammonium chloride.

8. The aqueous antimicrobial coating composition of claim 1, consisting essentially of 0.75 wt. % dimethyloctadecyl[3-(trihydroxysilyl)propyl]ammonium chloride; 0.12 wt. % 3-chloropropyltrimethoxysilane; 7.31 wt. % 3-aminopropyltriethoxysilane; 0.045 wt. % triethanolamine; remainder water.

9. The aqueous antimicrobial coating composition of claim 1, consisting essentially of 0.75 wt. % dimethyloctadecyl[3-(trihydroxysilyl)propyl]ammonium chloride; 0.15 wt. % 3-chloropropyltrimethoxysilane; 7.31 wt. % 3-aminopropyltriethoxysilane; and 0.045 wt. % triethanolamine; remainder water.

10. The aqueous antimicrobial coating composition of claim 1, consisting essentially of 0.75 wt. % dimethyloctadecyl[3-(trihydroxysilyl)propyl]ammonium chloride; 0.27 wt. % 3-chloropropyltrimethoxysilane; 7.31 wt. % 3-aminopropyltriethoxysilane; 0.045 wt. % triethanolamine; remainder water.

11. A method of forming an antimicrobial coating on a surface, the method comprising:
   (a) applying an aqueous antimicrobial coating composition to the surface, the aqueous antimicrobial coating composition comprising:
      (i) a mixture from about 0.1 wt. % to about 1.0 wt. % of dimethyloctadecyl[3-(trihydroxysilyl)propyl]ammonium chloride (DMOD), 3-chloropropyltrimethoxysilane (CPTMS), and from about 2.5 wt. % to about 12.5 wt. % 3-aminopropyltriethoxysilane (APTES) in water; and
      (ii) optionally, at least one organic amine having a structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12; and
   (b) allowing the aqueous antimicrobial coating composition to dry on the surface under ambient conditions, or drying the aqueous antimicrobial coating composition on the surface under heated conditions, to form the antimicrobial coating on the surface;
   wherein the aqueous antimicrobial coating composition, prior to applying to the surface, exhibits an absorbance at 600 nm of less than about 0.2 after 4-weeks of ambient storage.

12. The method of claim 11, wherein the at least one organic amine is present at from about 0.01 wt. % to about 1.0 wt. %, based on the total weight of the aqueous antimicrobial coating composition.

13. The method of claim 11, wherein the at least one organic amine comprises triethanolamine.

14. The method of claim 11, comprising 0.045 wt. % triethanolamine.

15. The method of claim 11, comprising from about 0.01 wt. % to about 0.5 wt. % 3-chloropropyltrimethoxysilane.

16. The method of claim 11, comprising 0.5 wt. % dimethyloctadecyl[3-(trihydroxysilyl)propyl]ammonium chloride.

17. The method of claim 11, comprising 0.75 wt. % dimethyloctadecyl[3-(trihydroxysilyl)propyl]ammonium chloride.

18. The method of claim 11, wherein the applying comprises spray application of the aqueous antimicrobial coating composition to the surface.

19. The method of claim 18, wherein the spray application further comprises electrostatic spraying.

20. A method of stabilizing a high pH aqueous antimicrobial coating composition comprising from about 0.1 wt. % to about 1.0 wt. % dimethyloctadecyl[3-(trihydroxysilyl)propyl]ammonium chloride (DMOD); from about 1.0 wt. % to about 15.0 wt. % 3-aminopropyltriethoxysilane (APTES); and from about 0.01 wt. % to about 1.0 wt. % triethanolamine (TEA) in water comprises adding from about 0.01 wt. % to about 0.5 wt. % 3-chloropropyltrimethoxysilane (CPTMS) to the aqueous coating composition, wherein the aqueous coating composition resulting therefrom exhibits an absorbance at 600 nm of less than about 0.2 after 4-weeks of ambient storage.

\* \* \* \* \*